(12) United States Patent
Chen et al.

(10) Patent No.: US 10,399,931 B2
(45) Date of Patent: Sep. 3, 2019

(54) OCTAHYDROANTHRACENE COMPOUND, PREPARATION METHOD AND APPLICATION THEREOF

(71) Applicants: SHANDONG XINHUA PHARMACEUTICAL CO., LTD., Zibo (CN); SHENYANG PHARMACEUTICAL UNIVERSITY, Shenyang (CN)

(72) Inventors: Guoliang Chen, Shenyang (CN); Zhonghui Zheng, Zibo (CN); Libo Zou, Shenyang (CN); Daiming Zhang, Zibo (CN); Chunling Yuan, Shenyang (CN); Fulong Ren, Zibo (CN); Xuefei Bao, Shenyang (CN); Jinheng Gao, Shenyang (CN); Linbo Zhou, Shenyang (CN); Wuhong Fang, Shenyang (CN)

(73) Assignees: SHANDONG XINHUA PHARMACEUTICAL CO., LTD., Zibo (CN); SHENYANG PHARMACEUTICAL UNIVERSITY, Shenyang (CN)

( * ) Notice: Subject to any disclaimer, the term of this patent is extended or adjusted under 35 U.S.C. 154(b) by 0 days.

(21) Appl. No.: 16/084,979

(22) PCT Filed: Mar. 23, 2017

(86) PCT No.: PCT/CN2017/077877
§ 371 (c)(1),
(2) Date: Sep. 14, 2018

(87) PCT Pub. No.: WO2017/181811
PCT Pub. Date: Oct. 26, 2017

(65) Prior Publication Data
US 2019/0071393 A1    Mar. 7, 2019

(30) Foreign Application Priority Data

Apr. 20, 2016   (CN) .......................... 2016 1 0247724

(51) Int. Cl.
| | |
|---|---|
| C07C 275/38 | (2006.01) |
| C07C 2/86 | (2006.01) |
| C07C 201/08 | (2006.01) |
| C07C 209/36 | (2006.01) |
| C07C 231/02 | (2006.01) |
| C07C 269/04 | (2006.01) |
| C07C 271/28 | (2006.01) |
| C07C 273/18 | (2006.01) |
| C07C 303/38 | (2006.01) |
| C07C 311/48 | (2006.01) |
| C07D 211/62 | (2006.01) |
| C07D 295/195 | (2006.01) |
| A61K 31/167 | (2006.01) |
| C07C 259/10 | (2006.01) |
| C07C 233/65 | (2006.01) |
| C07C 233/80 | (2006.01) |

(52) U.S. Cl.
CPC .......... *C07C 275/38* (2013.01); *A61K 31/167* (2013.01); *C07C 2/861* (2013.01); *C07C 201/08* (2013.01); *C07C 209/36* (2013.01); *C07C 231/02* (2013.01); *C07C 233/65* (2013.01); *C07C 233/80* (2013.01); *C07C 259/10* (2013.01); *C07C 269/04* (2013.01); *C07C 271/28* (2013.01); *C07C 273/1809* (2013.01); *C07C 303/38* (2013.01); *C07C 311/48* (2013.01); *C07D 211/62* (2013.01); *C07D 295/195* (2013.01); *C07C 2603/22* (2017.05); *C07C 2603/24* (2017.05)

(58) Field of Classification Search
CPC ..... C07C 275/38; C07C 2/861; C07C 201/08; C07C 209/36; C07C 231/02; C07C 271/28; C07C 273/1809; C07C 303/38; C07C 311/48; C07C 2603/22; C07D 211/62; C07D 295/195
See application file for complete search history.

(56) References Cited

U.S. PATENT DOCUMENTS

| | | | | |
|---|---|---|---|---|
| 4,936,121 | A | * | 6/1990 | Goto ...................... A01N 43/90 504/178 |
| 2015/0179941 | A1 | * | 6/2015 | Miyata ................. C07D 333/76 257/40 |

FOREIGN PATENT DOCUMENTS

| | | | |
|---|---|---|---|
| CN | 101855199 | A | 10/2010 |
| CN | 102329246 | A | 1/2012 |
| CN | 104761469 | A | 7/2015 |
| WO | 2005058803 | A1 | 6/2005 |
| WO | WO-2005058803 | A1 * | 6/2005 ........... C07C 233/80 |

OTHER PUBLICATIONS

Definition of Thiol—https://www.qmul.ac.uk/sbcs/iupac/class/ Glossary of Class Names of Organic Compounds and Reactive Intermediates Based on Structure (IUPAC Recommendations 1994). (Year: 1994).*
Definition of Amino—https://www.collinsdictionary.com/us/dictionary/english/amino_1 Webster's New World College Dictionary, 4th Edition. Copyright© 2010 by Houghton Mifflin Harcourt. (Year: 2010).*

(Continued)

*Primary Examiner* — Alexander R Pagano
(74) *Attorney, Agent, or Firm* — Gokalp Bayramoglu

(57) ABSTRACT

An octahydroanthracene compound having the structure shown in formula (I) and (II), preparation method and application thereof are disclosed. The octahydroanthracene compound has a good therapeutic effect on tumors and neurodegenerative diseases. The preparation of the octahydroanthracene compound is mainly carried out by using benzene as a starting material, and being subjected to Friedel-Crafts reaction, nitration, reduction, (sulfo-) amide formation, reduction, urea formation or amide formation, thus obtaining a target compound.

14 Claims, 2 Drawing Sheets

(56) References Cited

OTHER PUBLICATIONS

Definition of Sulfone—https://www.qmul.ac.uk/sbcs/iupac/class/ Glossary of Class Names of Organic Compounds and Reactive Intermediates Based on Structure (IUPAC Recommendations 1994) (Year: 1994).*

Definition of Sulfoxide—https://www.qmul.ac.uk/sbcs/iupac/class/ Glossary of Class Names of Organic Compounds and Reactive Intermediates Based on Structure (IUPAC Recommendations 1994) (Year: 1994).*

M. Kazmi et al., 74 Bioorganic Chemistry, 134-144 (2017) (Year: 2017).*

C. Yuan et al., 1865 Biochimica et Biophysica Acta, Molecular Basis of Disease, 161-180 (2019) (Year: 2019).*

Hiroyuki, K. et al. "Structure-Activity Relationships of Aromatic Amides with Retinoidal Activity" Journal of Medicinal Chemistry, vol. 31, No. 11, Dec. 31, 1988, pp. 2182-2192.

Paige E. Cramer et al. "ApoE-Directed Therapeutics Rapidly Clear β-Amyloid and Reverse Deficits in AD Mouse Models", Science, vol. 335, Mar. 23, 2012, pp. 1503-1506.

\* cited by examiner

Y-maze

Morris water maze

OCTAHYDROANTHRACENE COMPOUND, PREPARATION METHOD AND APPLICATION THEREOF

CROSS REFERENCE TO RELATED APPLICATIONS

This application is the national phase entry of international Application No. PCT/CN2017/077877, filed on Mar. 23, 2017, which is based upon and claims priority to Chinese Patent Application No. 201610247724.5, filed on Apr. 20, 2016, the entire contents of which are incorporated herein by reference.

TECHNICAL FIELD

The present invention belongs to the technical field of medicine and relates to a series of octahydroanthracene compounds, preparation methods and applications thereof.

BACKGROUND

Alzheimer's disease (AD) is a degenerative disease of the chronic central nervous system and is the most common type of senile dementia. The early clinical manifestations are mainly the patients' decreased memory and decline in self-care ability, which ultimately leads to cognitive dysfunction and loss, neurobehavioral abnormality and complete loss of self-care ability. The course of disease is generally 6 to 12 years, and the patient often dies from concurrent infections. In 2010, Alzheimer's Disease International (ADI) reported and estimated that there are approximately 35.6 million people suffering from dementia worldwide, accounting for around 0.5% of the world's total population, the prevalence of dementia in people aged 60 years and over is 5%-7%, and is expected to reach 115.4 million in 2050. The total estimated expenses for treatment of dementia worldwide reached up to $604 billion in 2010, which is estimated to increase by 85% by 2030. According to the World Health Organization, by 2020, AD will become the fourth disease in China's disease burden. AD not only seriously affects patient's physical health and quality of life, but also imposes a heavy burden on the patient's family and on society. The elucidation of etiology and pathogenesis of AD, and the study of preventive and therapeutic methods have become an urgent medical and social problem to be solved.

Neuropathological features of AD include diffuse brain atrophy, deposition of extracellular neuritic plaques or senile plaques (SP), intracellular neurofibrillary tangle (NFT), and neuronal loss, accompanying with granulovacuolar degeneration and meningeal vascular amyloid degeneration, etc.

The etiology and pathogenesis of AD is very complicated, although the study of the etiology and pathogenesis of AD have been reported a lot, the pathogenesis of AD has not been fully elucidated so far, which is related to the complexity of the pathogenesis and the interaction of multiple factors. There are many hypotheses about the pathogenesis of AD, including cholinergic theory, β-Amyloid peptides (Aβ) deposition hypothesis, oxidative stress hypothesis, inflammation and immunology theory, microtubule-associated protein dysfunction hypothesis, insulin hypothesis, metal ion metabolism disorder hypothesis, gene mutation hypothesis, among others.

The amyloid cascade hypothesis has always occupied the main position of the pathogenesis of AD. The hypothesis posits that the abnormal metabolism of amyloid protein precursor (APP) in the brain increases the production of amyloid β-protein and decreases the degradation of amyloid β-protein, causing a large number of Aβ accumulation, and the excess Aβ accumulation forms amyloid plaques (i.e., senile plaques, SP), resulting in neurotoxicity. Therefore, AD therapeutic drugs targeting Aβ have become one of the main directions of clinical research.

Aβ Production and Metabolism

APP is an Aβ precursor protein. Under normal circumstances, APP has two hydrolysis pathways in human body. One is the non-Aβ generation pathway. APP is mainly hydrolyzed by α-secretase into a soluble APP alpha (soluble APP, sAPPα) containing partial Aβ sequence and a C83 carboxy-terminal fragment, and the latter is further degraded by γ-secretase. At present, sAPPα is known to have neurotrophic effects, and is capable of promoting the development of nerve cells and plays a role in neuronal cell protection by reducing intracellular $Ca^{2+}$ concentration, which is related to learning and memory functions. However, an sAPPα deficiency has not been proven to be directly related to the pathogenesis of AD. This pathway is the main pathway for APP metabolism. The other is the Aβ generation pathway. APP is first hydrolyzed by β-secretase into sAPPβ and a C99 carboxy-terminal fragment, and the latter is further degraded by γ-secretase to produce Aβ42 or Aβ40. However, Aβ42 is more prone to form β-sheet structure and is easier to aggregate into oligomers and fibers, which is more cytotoxic than Aβ40. Meanwhile, recent studies have confirmed that soluble oligomeric Aβ is more neurotoxic than mature insoluble fibrous Aβ. There are many toxic mechanisms of Aβ. For example, Aβ can induce the brain neurons to produce oxygen free radicals, thus destroying the structure of nerve cell membranes, causing the function to be abnormal. In addition, Aβ may alter the distribution of neurotransmitters and signaling molecules. Aβ can also increase intracellular free calcium ions, and through various pathways to trigger mitochondrial dysfunction, axoplasmic transport dysfunction, and cause neuronal loss, etc. However, some researchers believe that Aβ is not a predictor of human death but a protective response to neuronal damage. At physiological concentrations of nanomolar, Aβ can be used as a nutritional factor with nutritional and neuroprotective effects. Zou et al. demonstrated that, at nanomolar concentrations Aβ42 monomer can be used as a nutrient factor to inhibit metal-induced oxidative stress. Some researchers also believe that in AD patients, the increase of Aβ production may exceed a physiological concentration, making it possible to acquire neurotoxic effects. Although the effect of Aβ in AD is still vague, when the concentration of Aβ increases to a certain level, the toxic effect is greater than the protective effect.

There are two main pathways for the Aβ metabolism: the enzymatic degradation pathway and the receptor-mediated transport out of the brain pathway.

To this end, the development of drugs targeting key links such as the production, aggregation and clearance of Aβ has become a research hotspot. The drugs targeting Aβ are mainly divided into the following categories:

Reduction of the Generation of Aβ

α-Secretase Agonists

At present, there are few reports on α-secretase research. α-secretase is a member of the family of a disintegrin and metalloproteinase (ADAM), up-regulating the activity thereof not only reduces the generation of Aβ, but also increases the generation of sAPPα with neuroprotective effects, which has potential AD therapeutic effects. The activity of α-secretase is regulated by protein kinase C (PKC) protein phosphorylation signal transduction pathway. Directly stimulating the activity of α-secretase or indirectly stimulating the activity of PKC and PKC pathway-related proteins can achieve to up-regulate the activity of α-secretase. Studies have found that certain statins, vitamin A drugs and neuropeptides (such as pituitary adenylate cyclase-activating peptide) can increase α-secretase activity or PKC activity.

β-Secretase Inhibitors

It is currently believed that there are two different β-secretases, BACE1 (β-site APP-cleaving enzyme 1) and BACE2. BACE1 has all the activities of β-secretase and is a key enzyme for Aβ generation. BACE2 is a homologous enzyme of BACE1, mainly distributed in the heart, kidney and placenta, but rarely distributed in brain tissue, which can compete with BACE1 for APP site, but cannot catalyze and form intact Aβ. Thus, it can be inferred that BACE2 does not play an important role in the generation of Aβ. Therefore, selective BACE1 inhibitors have potential AD therapeutic effects, but there are two major constraints: first of all, BACE1 has a very important physiological effect, and inhibiting the activity thereof may produce obvious toxic side effects. In addition, BACE1 has a larger active area, and the compounds required to inhibit the BACE1 activity is large in volume, while the large-volume compounds are difficult to pass through the blood-brain barrier. Because of these constraints, only a few compounds among the many BACE1 inhibitors have entered clinical trials.

γ-Secretase Inhibitors

γ-secretase acts as a key enzyme that directly catalyzes the generation of Aβ, inhibition of the γ-secretase activity is a very attractive target for the treatment of AD. Studies have found that in addition to acting on APP-related substrates, γ-secretase can also affect various physiological functions such as embryonic development, hematopoiesis, cell adhesion, and cell-cell interaction through the Notch signal transduction pathway, and non-specific inhibition of the γ-secretase activity can produce many significant and serious side effects. The focus of current research is mainly on finding highly selective γ-secretase inhibitors or regulators. In addition, some non-steroidal anti-inflammatory drugs (such as ibuprofen, indomethacin and sulindac sulfide, flurbiprofen, etc.) have the function of γ-secretase regulators. Among them, the results of phase II clinical trials of flurbiprofen (also known as tarenflurbil or MPC-7869) were gratifying. However, in the phase III clinical trials, completely negative results were obtained. It is analyzed that the reasons may be related to the limited inhibition of tarenflurbil to γ-secretase activity and the poor permeability of blood-brain barrier.

Drugs for Inhibition of Aβ Aggregation

Aβ aggregation is a multi-step process involving multiple intermediates that includes oligomers and fibrils. Tramiprosate is a polysaccharide analogue that can combine with Aβ to block and inhibit the formation of plaques. The results of phase II clinical trials showed that long-term use of tramiprosate is safe and can reduce Aβ42 in the cerebrospinal fluid. However, tramiprosate did not show significant effects in the phase III clinical trial and the test has been discontinued.

In addition, studies have found that metal ions in the brain, such as zinc ions and copper ions, can promote the polymerization of soluble Aβ and stabilize the Aβ polymer. PBT1 (clioquinol) is a metal complexing agent that can affect the interaction of copper and zinc ions with Aβ. Phase II clinical trials have found that the PBT1 is well tolerated, can effectively reduce the Aβ concentrations in plasma and reduce cognitive deterioration of AD patients (especially patients with severe AD). However, due to the manufacturing process, some high toxicity impurities remain in PBT1, which limits further application of PBT1. PBT2 is an analogue of PBT1, which shows anti-Aβ oligomerization effect of PBT2 is the same as or superior than anti-Aβ oligomerization effect of PBT1 in animal experiments. PBT2 has also entered the phase II clinical trial and found that PBT2 is safe and well tolerated, can effectively reduce the concentration of Aβ1-42 in the cerebrospinal fluid and has a certain improvement effect on the two executive functions of AD patients.

Promotion of the Clearance of Aβ

Two pathways of increasing the enzymatic degradation of Aβ and up-regulating receptor-mediated Aβ transport out of the brain are included.

Application of Retinoic Compounds in the Treatment of AD

Receptor subtype-selective retinoic compounds have good targeting properties and can reduce the toxic side effects of retinoic compounds, and thus are one of the main research directions of retinoic compounds. The receptor subtype-selective drugs currently on the market include tamibarotene and bexarotene. It has been reported that bexarotene can rapidly clear the β-amyloid protein deposited in the brain of laboratory mice with Alzheimer's symptoms-like disease, and is considered to have great potential for the treatment of Alzheimer's disease (Science, 2012, 335(6075): 1503-1506.).

SUMMARY

The present invention provides some octahydroanthracene compounds which promote the clearance of Aβ amyloid plaques and reduce the deposition of Aβ amyloid plaques with high efficiency and extremely low toxicity. The bioactivity experiments found that continuous oral administration of these octahydroanthracene compounds for 7-15 days can significantly improve spatial learning and memory, image recognition memory and impairment of long-term learning and memory of APP/PS1 double transgenic Aβ model mice of 8 months old and can make various learning and memory scores return to the level of the normal control group. The cerebral cortex and hippocampal β-amyloid deposition experiments of APP/PS1 double transgenic AD model mice found that these octahydroanthracene compounds can promote the clearance of Aβ amyloid plaques and reduce the deposition of Aβ amyloid plaques, the clearance rate can reach about 67%. Preliminary safety evaluation: the mice were intragastrically administered with compound OAB-14 5000 mg/kg, which is 30 times of the pharmacodynamic dose; no visible adverse reactions were observed in the mice, and the mice were in good condition. Donepezil was used as the positive control drug, and the 8-month-old. APP/PS1 double transgenic AD model mice were used as the experimental models. The results showed that whether consecutively administered for 14 days or for 3 months, OAB-14 could dose-dependently improve multiple learning and memory disorders of model animals in new object discrimination experiments Y-maze experiments, Morris water maze experiments, nesting experiments and social activity experiments; thereby increasing cognitive function, social interaction, self-care ability, and present a good dose-effect relationship. In particular, the high-dose group was significantly stronger than the donepezil group and completely recovered to the level of the blank group, and no changes were observed in the main organ tissue sections compared with the blank group. While improving learning and memory, and reducing β-amyloid protein deposition, the organ indexes of heart, liver, spleen and kidney were not abnormal. Therefore, such octahydroanthracene compounds can be used for the treatment of neurodegenerative diseases (such as Alzheimer's disease, Parkinson's disease, etc.), tumors, etc.

The structural formula of the octahydroanthracene compound of the present invention is as shown in (I) or (II):

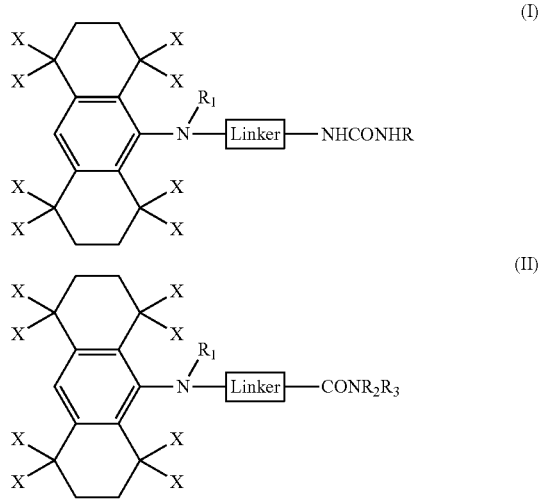

wherein X is H or C1-C6 alkyl group;

Linker is a substituted/unsubstituted C6-C10 aroyl (sulfonyl) group or a substituted/unsubstituted heteroaroyl (sulfonyl) group; and wherein the substituent of the substituted. C6-C10 aroyl (sulfonyl) group or substituted heteroaroyl (sulfonyl) group is a C1-C6 alkyl group, a C1-C6 alkoxy group, a halogen, an amino group, a nitro group, a mercapto group, a thioether, a sulfone, a sulfoxide or an aminoalkoxy group;

$R_1$ is hydrogen or C1-C6 alkyl group;

R is a nitrogen- or nitrogen-free structural fragment;

$R_2$, $R_3$ may be hydrogen, nitrogen- or nitrogen-free structural fragments;

and wherein the nitrogen-free structural fragment is C1-C20 alkyl group;

the structure of the nitrogen-structural fragment is:

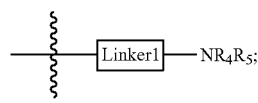

and wherein the Linker1 is a C2-C6 linear or branched alkyl group, and the $NR_4R_5$ is a primary amine or secondary amine.

The present invention preferably has a compound having the structural formula of (I) or (II):

wherein X is H or C1-C6 alkyl group;

Linker is a substituted/unsubstituted phenyl group, pyridine, furan, pyrrole, thiazole or thiophene; wherein the substituent is a C1-C6 alkyl group, a C1-C6 alkoxy group;

$R_1$ is hydrogen or C1-C6 alkyl group;

R is a nitrogen- or nitrogen-free structural fragment;

$R_2$, $R_3$ may be hydrogen, nitrogen- or nitrogen-free structural fragments;

and wherein the nitrogen-free structural fragment is C1-C20 alkyl group;

the structure of the nitrogen-structural fragment is:

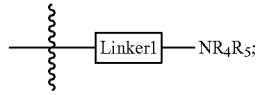

and wherein the Linker1 is a C2-C6 linear or branched alkyl group, and the $NR_4R_5$ is a primary amine or secondary amine.

The present invention preferably has a compound having the structural formula of (I) or (II):

wherein X is H or C1-C6 alkyl group;

Linker is a substituted/unsubstituted C6-C10 aroyl (sulfonyl) or a substituted/unsubstituted heteroaroyl (sulfonyl) group; and wherein the substituent of the substituted C6-C10 aroyl (sulfonyl) group or substituted heteroaroyl (sulfonyl) group is a C1-C6 alkyl group, a C1-C6 alkoxy group, a halogen, an amino group, a nitro group, a mercapto group, a thioether, a sulfone, a sulfoxide or an aminoalkoxy group;

$R_1$ is hydrogen or C1-C6 alkyl group;

R is a nitrogen- or nitrogen-free structural fragment;

$R_2$, $R_3$ may be hydrogen, nitrogen- or nitrogen-free structural fragments;

and wherein the nitrogen-free structural fragment is C1-C10 alkyl group;

the structure of the nitrogen-structural fragment is:

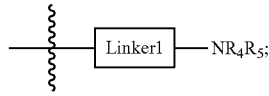

and wherein the Linker1 is a C2-C6 linear or branched alkyl group;

the $NR_4R_5$ is a primary amine or secondary amine, which selected from but not limited to:

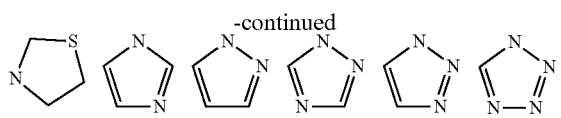

The octahydroanthracene compound of the present invention and the pharmaceutically acceptable salts thereof are selected from, but not limited to:

4-[(1,1,4,4,5,5,8-octamethyl-1,2,3,4,5,6,7,8-octahydro-9-anthryl) carbamoyl] methyl benzoate;
4-[(1,1,4,4,5,5,8,8-octamethyl-1,2,3,4,6,7,8-octahydro-9-anthryl) carbamoyl] benzoic acid;
N-hydroxy-4-[(1,1,4,4,5,5,8,8-octamethyl-1,2,3,4,5,6,7,8-octahydro-9-anthryl) carbamoyl] benzamide;
N-(2-aminophenyl)-4-[(1,1,4,4,5,8,8-octamethyl-1,2,3,4,5,6,7,8-octahydro-9-anthryl) carbamoyl] benzamide;
N-[2-(N,N-diethylamino)ethyl-4-(1,1,4,4,5,5,8,8-octamethyl-1,2,3,4,5,6,7,8-octahydro-9-anthryl) carbamoyl] benzamide;
N-(2-amino) ethyl-4-[(1,1,4,4,5,5,8,8-octamethyl-1,2,3,4,5,6,7,8-octahydro-9-anthryl) carbamoyl] benzamide;
N-[2-(N,N-dimethylamino)]ethyl-4-[(1,1,4,4,5,5,8,8-octamethyl-1,2,3,4,5,6,7,8-octahydro-9-anthryl) carbamoyl] benzamide;
N-(2-hydroxyphenyl)-4-[(1,1,4,4,5,5,8-octamethyl-1,2,3,4,5,6,7,8-octahydro-9-anthryl) carbamoyl] benzamide;
4-[(1,1,4,4,5,5,8,8-octamethyl-1,2,3,4,5,6,7,8-octahydro-9-anthryl) carbamoyl] aniline;
4-[(1,1,4,4,5,5,8,8-octamethyl-1,2,3,4,5,6,7,8-octahydro-9-anthryl) carbamoyl] ethyl phenylcarbamate;
4-[(1,1,4,4,5,5,8,8-octamethyl-1,2,3,4,5,6,7,8-octahydro-9-anthryl) carbamoyl] phenylcarbamoyl-1-morpholine;
1-(2-aminophenyl)-3-{4-[(1,1,4,4,5,5,8,8-octamethyl-1,2,3,4,5,6,7,8-octahydro-9-anthryl) carbamoyl] phenyl} urea;
1-(2-amino) ethyl-3-{4-[(1,1,4,4,5,5,8,8-octamethyl-1,2,3,4,5,6,7,8-octahydro-9-anthryl) carbamoyl] phenyl} urea;
1-(2-hydroxy) ethyl-3-{4-[(1,1,4,4,5,5,8,8-octamethyl-1,2,3,4,5,6,7,8-octahydro-9-anthryl) carbamoyl] phenyl} urea;
1-(3-hydroxy)propyl-3-{4-[(1,1,4,4,5,5,8,8-octamethyl-1,2,3,4,5,6,7,8-octahydro-9-anthryl) carbamoyl] phenyl} urea;
N,N-dimethylsulfonyl-4-[(1,1,4,4,5,5,8,8-octamethyl-1,2,3,4,5,6,7,8-octahydro-9-anthryl) carbamoyl] aniline;
1-(4-carboxypropyl)-3-{4-[(1,1,4,4,5,5,8,8-octamethyl-1,2,3,4,5,6,7,8-octahydro-9-anthryl) carbamoyl] phenyl} urea;
N-{4-[(1,1,4,4,5,5,8,8-octamethyl-1,2,3,4,5,6,7,8-octahydro-9-anthryl) carbamoyl] phenylcarbamoyl}-4-piperidinyl formic acid;
4-[(1,1,4,4,5,5,8,8-octamethyl-1,2,3,4,5,6,7,8-octahydro-9-anthryl) carbamoyl] methyl phenylcarbamate;
1-(2-hydroxyphenyl)-3-{4-[(1,1,4,4,5,5,8,8-octamethyl-1,2,3,4,5,6,7,8-octahydro-9-anthryl) carbamoyl] phenyl} urea;
1-[2-(N,N-diethylamino)]ethyl-3-{4-[(1,1,4,4,5,5,8,8-octamethyl-1,2,3,4,5,6,7,8-octahydro-9-anthryl) carbamoyl] phenyl} urea;
1-[2-(N,N-dimethylamino)]ethyl-3-{4-[(1,1,4,4,5,5,8,8-octamethyl-1,2,3,4,5,6,7,8-octahydro-9-anthryl) carbamoyl] phenyl} urea;
1-hydroxy-3-{4-[(1,1,4,4,5,5,8,8-octamethyl-1,2,3,4,5,6,7,8-octahydro-9-anthryl) carbamoyl] phenyl} urea;
4-[(1,1,4,4,5,5,8,8-octamethyl-1,2,3,4,5,6,7,8-octahydro-9-anthryl) carbamoyl] phenyl carbamic acid-O-amino ester.

The synthesis route of the octahydroanthracene compound of the present invention is as follows: wherein a compound in which X is a methyl group is synthesized, and the starting material is 2,5-dimethyl-2,5-hexanediol, through chlorination, Friedel-Crafts alkylation, nitration, reduction, and then amide is formed, hydrolysis and re-formation of amide, or after the first amide formation, reduction, and then urea is formed:

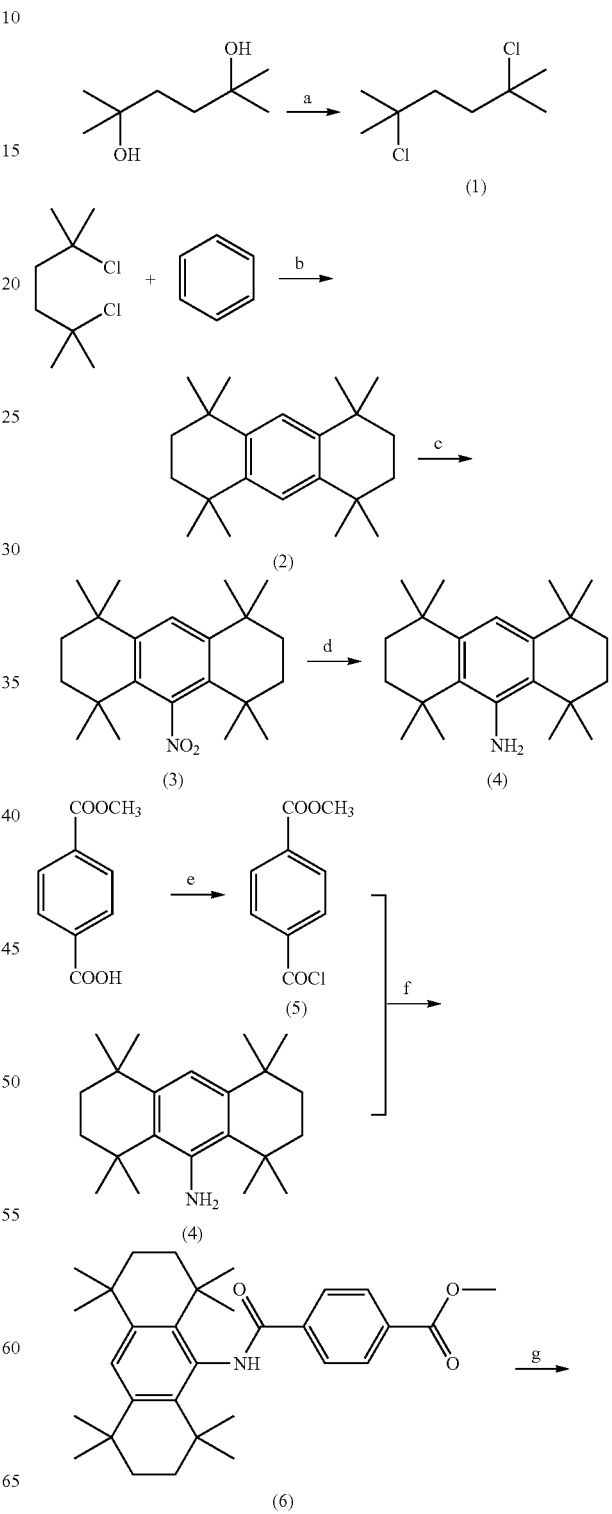

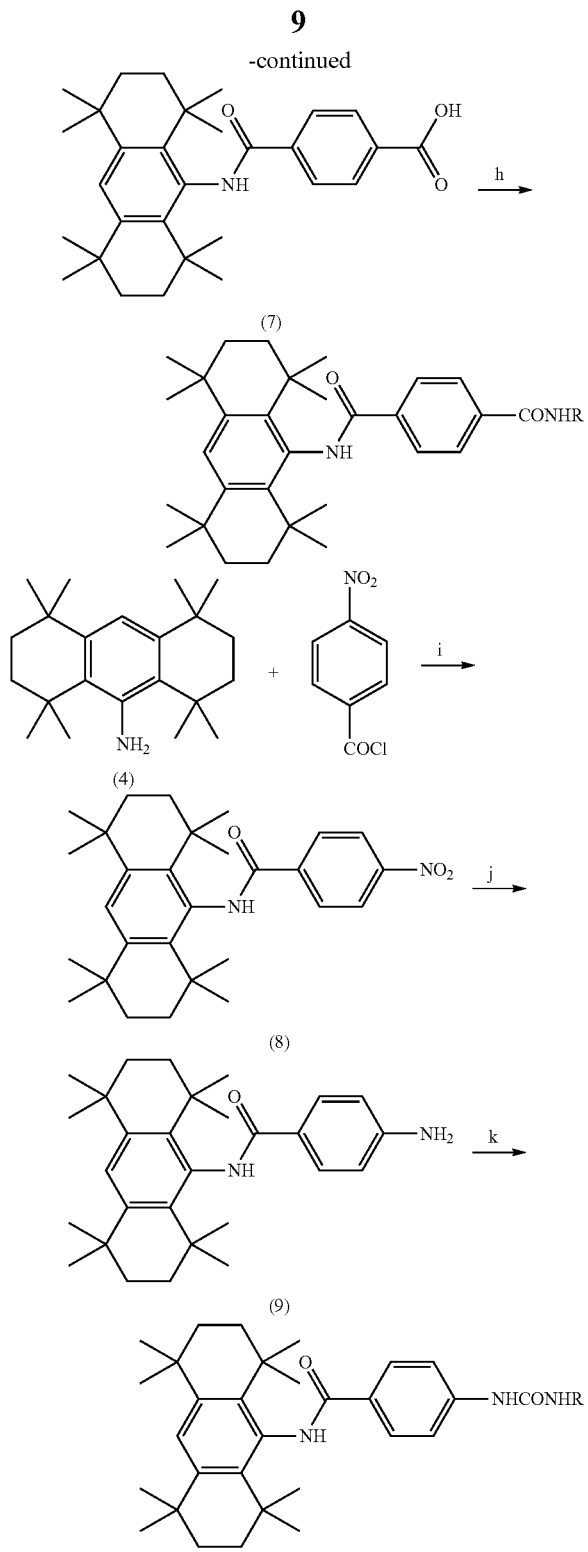

Reaction conditions of each step: a. con. HCl, 80° C., 1 h; b. AlCl₃, DCM, rt, 2 h; c. CH₃COOH, con. HNO₃+con. H₂SO₄, DCM, 40° C., 3 h; d. Sn/HCl (g), con. HCl, ethanol; e. SOCl₂, 1d DMF, reflux, 3 h; f. DMAP, Py, xylol, reflux, 12 h; g. 8% NaOH(aq), CH₃OH, reflux, 23 h. SOCl₂/DCM, reflux, 3 h, TEA, primary amine; i. DMAP, Py, xylol, reflux, 12 h; j. Pd—C/H₂, C₂H₅OH, THF, 30° C., 25 h; k. BTC/DCM, TEA, amine.

DETAILED DESCRIPTION OF THE EMBODIMENTS

Figure 1:
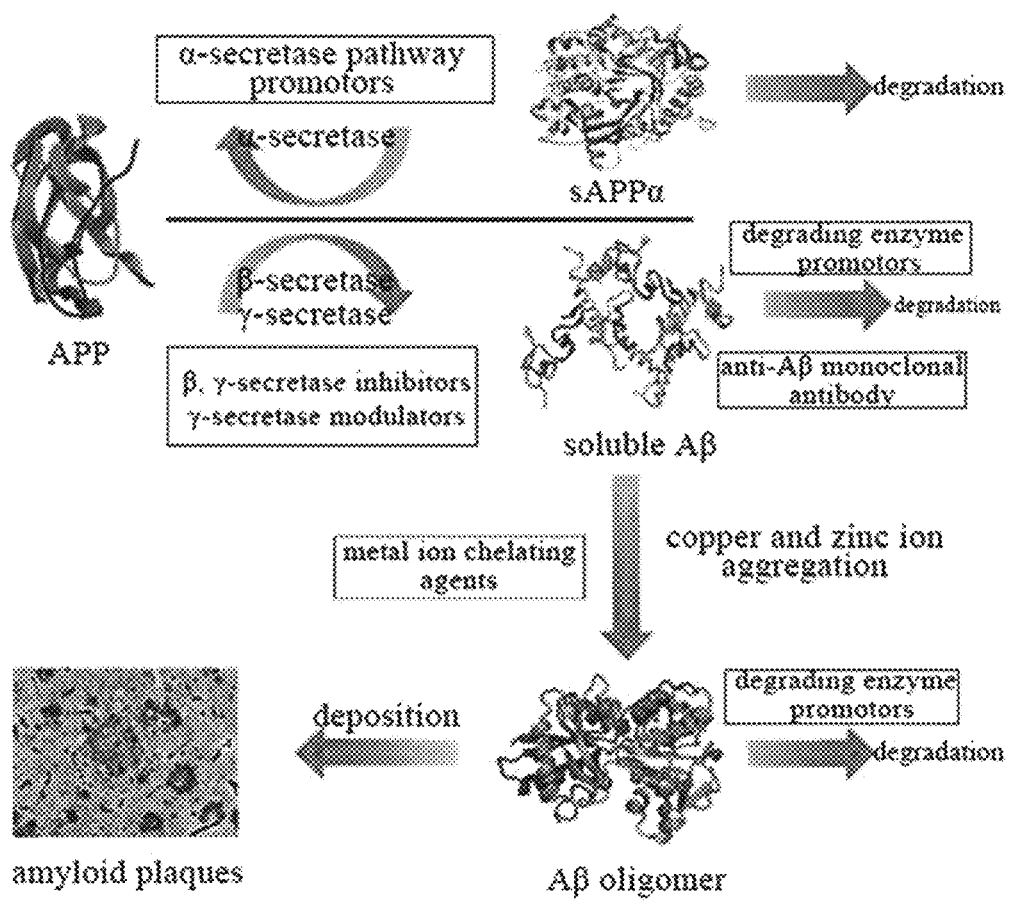
FIG. 1 is the treatment strategy for Aβ.
Figure 2:
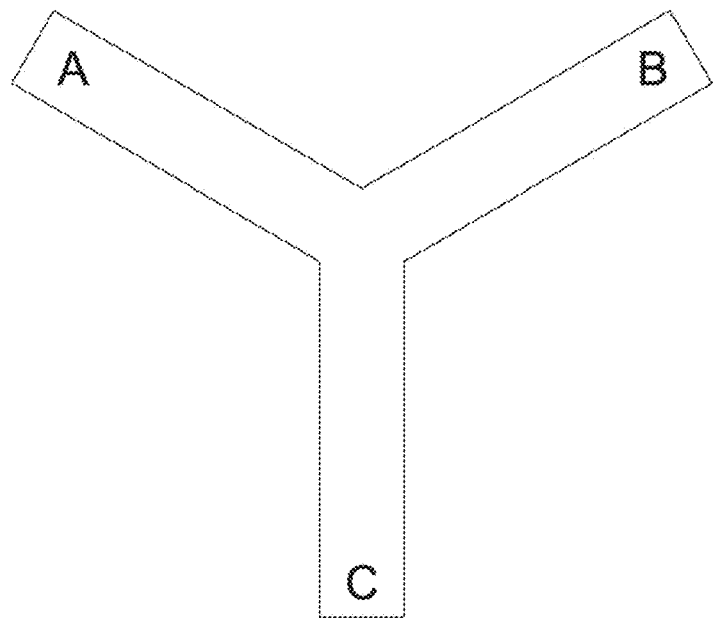
FIG. 2 is the experimental device of Y-maze.
Figure 3:
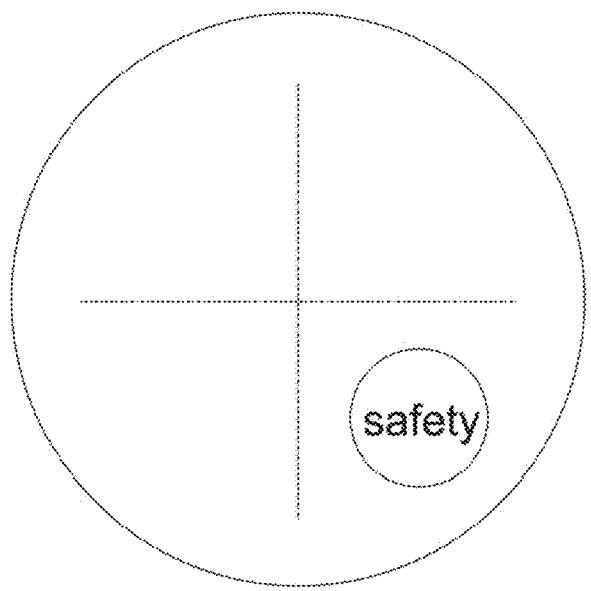
FIG. 3 is the experimental device of Morris water maze.

The melting point of the octahydroanthracene compound was determined using a X-4 type digital display melting point apparatus, and the thermometer was uncorrected. Nuclear magnetic resonance $^1$H-NMR was measured using a Bruker ARX-300 or a 600 MHz NMR spectrometer with TMS as an internal standard. Liquid quality (LC-MS-ESI) was measured using an Agilent 1100 Series MSD Trap (SL) or the like. All the reagents used were analytical grade and were further purified.

Embodiment 1

Preparation of the Intermediate 1,1,4,4,5,5,8,8-octamethyl-1,2,3,4,5,6,7,8-octahydro-9-aminoanthracene Preparation of 1,1,4,4,5,5,8,8-octamethyl-1,2,3,4,5,6,7,8-octahydroanthracene (OA)

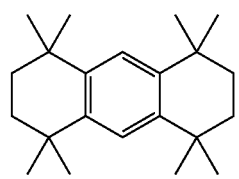 [SMILES: CC1(C)CCC(C)(C)c2cc3c(cc21)C(C)(C)CCC3(C)C]

Placing 2,5-dichloro-2,5-dimethylhexane (100 g, 0.546 mol) in a 1 L three-necked flask, and completely dissolving with 500 mL of dried dichloromethane (at room temperature); pipetting benzene (24.3 mL, 0.273 mol) into the above solution and stirring for 10 min; slowly adding anhydrous AlCl₃ (7.3 g, 0.0546 mol) in batches, reacting violently, the temperature did not change significantly, the color of the solution gradually deepened to dark brown and solid is precipitated; after reacting for 2 h, slowly pouring the reaction solution into a 2 L beaker containing 500 mL of ice-water mixture (pH was previously adjusted to acidity with concentrated hydrochloric acid), stirring for 1 h, then perform extraction with 1 L of dichloromethane; washing the organic layer with distilled water to neutralize, and then washing with a small amount of saturated aqueous NaCl solution, drying with anhydrous Na₂SO₄ for 3 h, then performing suction filtration, and evaporating the solvent to obtain 79 g of yellowish solids, with a yield of 97%. m.p. is 219-221° C. $^1$H-NMR (600 MHz, CDCl₃): δ(ppm) 7.18 (2H, s, Ar—H), 1.65 (8H, s, 4×CH₂), 1.26 (24H, s, 8×CH₃).

Embodiment 2

Preparation of 1,1,4,4,5,5,8,8-octamethyl-2,3,4,5,6,7,8-octahydro-9-nitroanthracene

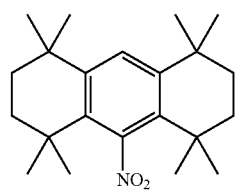 [SMILES: CC1(C)CCC(C)(C)c2c1cc1c(c2[N+](=O)[O-])C(C)(C)CCC1(C)C]

Placing OA (10 g, 33.5 mmol) in a 250 mL three-necked flask, completely dissolving with 130 mL of dichloromethane, adding 6.2 mL of glacial acetic acid at room temperature; slowly adding the mixed acid (placing concentrated nitric acid (4.6 mL, 67 mmol) in a 100 mL small beaker, slowly adding concentrated sulfuric acid (10.6 mL, 195 mmol) under an ice bath, stirring for 0.5 h for standby application) with a dropping funnel. After the addition is completed, raising the temperature to 40° C. and reacting for 3 h; slowly pouring the reaction solution into a 600 mL ice-water mixture, performing suction filtration, washing the residue to neutral, drying to obtain 6.9 g of yellow solids, and washing the filtrate to neutralize, drying with anhydrous magnesium sulfate, then performing suction filtration, evaporating the solvent to obtain 4.3 g of brown-red viscous substance; performing the column chromatographic separation (eluent: PE) to obtain 6.6 g of yellowish crystals, with a yield of 57%. m.p. is 269-270° C. $^1$H-NMR (600 MHz, CDCl$_3$): δ(ppm) 7.40 (1H, s, Ar—H), 1.72-1.61 (8H, m, 4×CH$_2$), 1.29 (12H, s, 4-CH$_3$), 1.28 (12H, s, 4×CH$_3$).

Embodiment 3

Preparation of 1,1,4,4,5,5,8,8-octamethyl-1,2,3,4,5,6,7,8-octahydro-9-aminoanthracene (OA-HY)

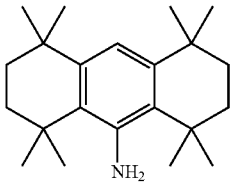 [SMILES: CC1(C)CCC(C)(C)c2c1cc1c(c2N)C(C)(C)CCC1(C)C]

Placing 1,1,4,4,5,5,8,8-octamethyl-1,2,3,4,5,6,7,8-octahydro-9-aminoanthracene (10 g, 29.1 mmol) in a 500 mL three-necked flask, adding tin particles (30 g, 252.7 mmol), 200 mL absolute ethanol, 10 mL, concentrated hydrochloric acid successively; introducing hydrogen chloride gas into the reaction solution gradually, reflux reacting for 3 h, then stopping introducing hydrogen chloride gas, having tin particles remained, cooling overnight. On the next day, a small amount of crystals was precipitated in the reaction solution. Adding a portion of methylene chloride to dissolve the crystals completely, then performing suction filtration, removing the tin particles, and evaporating the organic solvent; adding 500 mL of distilled water to the residue and stirring for 2 h, then performing suction filtration, and washing the residue to neutral, drying to obtain 8.97 g white solid, with a yield of 98.3%. m.p. is 246-248° C. LC-MS (ESI) m/z: 314.35 [M+H]$^+$. $^1$H-NMR (600 MHz, CDCl$_3$): δ(ppm) 6.81 (1H, s, Ar—H), 1.74-1.62 (8H, m, 4×CH$_2$), 1.48 (12H, s, 4×CH$_3$), 1.30 (12H, s, 4×CH$_3$).

Preparation of OAA Series Compounds

Preparation of 4-methoxycarbonylbenzoyl Chloride

Placing 10 g of crude monomethyl terephthalate in a 250 mL single-mouth flask, recrystallizing with 150 mL of methanol (anhydrous) and 60 mL of 5% hydrochloric acid; there were a small amount of insoluble matter, pouring the hot supernatant into a conical flask, cooling and crystallizing, performing suction filtration, washing the residue to neutralize, and drying to obtain 6.5 g of white crystals.

Placing monomethyl terephthalate (6.0 g, 33.3 mmol) in a 100 mL single-mouth flask, adding 30 mL of thionyl chloride and one drop of N,N-dimethylformamide, reflux reacting, 3 h later, evaporating the solvent under atmospheric pressure; adding cyclohexane (3×10 mL) to the residue, and evaporating the solvent to obtain 6.4 g of white solids, with a yield of 97%.

Embodiment 4

Preparation of 4-[(1,1,4,4,5,5,8,8-octamethyl-1,2,3,4,5,6,7,8-octahydro-9-anthryl) carbamoyl] methyl Benzoate (OAA-01)

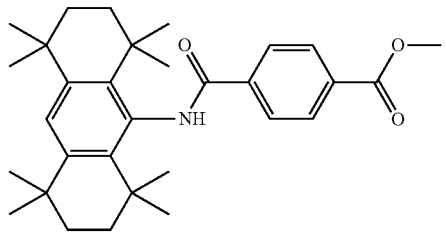

Placing OA-HY (1.0 g, 3.19 mmol) in a 50 mL single-mouth flask, adding 28 mL of dried xylene to dissolve the OA-HY completely; then adding p-dimethylaminopyridine (0.08 g, 0.65 mmol), dried pyridine (3.0 mL, 37.3 mmol), 4-methoxycarbonylbenzoyl chloride (1.27 g, 6.38 mmol) successively, and refluxed reacting for 12 h under argon gas protection; slowly reducing the temperature to 80° C., slowing dropping about 10 mL of methanol (anhydrous) to the reaction solution; then transferring this reaction solution to a 500 mL single-mouth flask, adding methanol (anhydrous) to about 250 mL, refluxing for 3 h, performing immediate filtration; washing the residue with distilled water and drying to obtain 1.25 g of white solids, with a yield of 82% m.p. is higher than 300° C. $^1$H-NMR (600 MHz, CDCl$_3$): δ(ppm) 8.20-8.18 (2H, d, J=8.4 Hz), 8.02-8.00 (2H, d, J=8.4 Hz), 7.54 (1H, s, —NH—CO—), 7.35 (1H, s, Ar—H), 3.97 (3H, s, —OCH$_3$), 1.83-1.46 (8H, m, 4×CH$_2$), 1.42 (6H, s, 2×CH$_3$), 1.32 (6H, s, 2×CH$_3$), 1.27 (6H, s, 2×CH$_3$), 1.25 (6H, s, 2×CH$_3$).

Embodiment 5

Preparation of 4-[(1,1,4,4,5,5,8,8-octamethyl-1,2,3,4,5,6,7,8-octahydro-9-anthryl) carbamoyl] benzoic Acid (OAA-02)

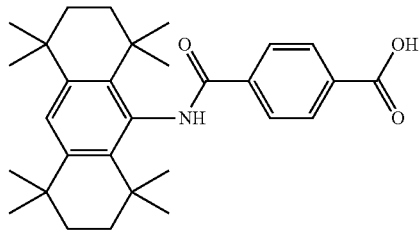 [SMILES: CC1(C)CCC(C)(C)c2c1cc1c(c2NC(=O)c2ccc(C(=O)O)cc2)C(C)(C)CCC1(C)C]

Placing OAA-01 (1.75 g, 3.68 mmol) in a 500 mL single-mouth flask, adding 70 mL of 8% sodium hydroxide aqueous solution, 175 mL of methanol (anhydrous) successively, refluxing for 8 h; adding additional 40 mL of 8% aqueous sodium hydroxide solution, refluxing for 15 h; performing suction filtration, and adjusting the pH of the filtrate to 6; performing suction filtration, washing the residue with distilled water for 3 times, drying to obtain 1.1 g of white solids; taking 0.75 g of the white solids to recrystallize with methanol and performing freezing crystallization in a refrigerator, performing suction filtration and drying to obtain 0.63 g of white solids, with a yield of 54%. m.p. is higher than 300° C. LC-MS (EST) m/z: 460.1 [M–H]$^-$, 462.4 [M+H]$^+$, 484.3 [M+Na]$^+$ 500.3 [M+K]$^+$. $^1$H-NMR (300 MHz, CD$_3$OD): δ(ppm) 8.21-8.17 (2H, d, J=8.7 Hz), 8.15-8.11 (2H, d, J=8.7 Hz), 7.42 (1H, s, Ar—H), 1.81-1.51 (8H, m, 4×CH$_2$), 1.45 (6H, s, 2×CH$_3$), 1.32 (6 s, 2×CH$_3$), 1.28 (6H, s, 2×CH$_3$), 1.24 (6H, s, 2×CH$_3$).

Embodiment 6

Preparation of N-hydroxy-4-[(1,1,4,4,5,5,8,8-octamethyl-1,2,3,4,5,6,7,8-octahydro-9-anthryl) carbamoyl] benzamide (OAA-03)

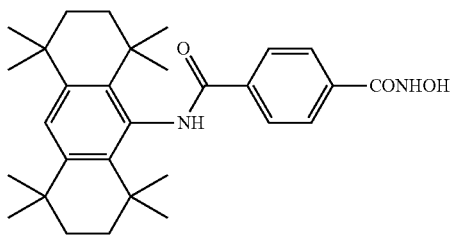

Adding OAA-02 (0.4 g, 0.868 mmol) to a 100 mL three-necked flask, adding 50 mL of dried THF; adding TEA (0.24 mL, 1.735 mmol) and adding dropwise ethyl chloroformate (0.17 mL, 1.735 mmol) under a condition of stirring and ice bath (4° C.), white smoke is formed; stirring for 30 min after the addition is completed, and the solution was milky white; slowly adding a small amount of hydroxylamine hydrochloride dissolved with methanol (0.12 g, 1.735 mmol) with a dropping funnel, and the addition is complete after 20 min; continuing to stir under the ice bath for 10 min; removing the ice bath, reacting at room temperature for 28 h; adding additional TEA (0.48 mL, 3.47 mmol) under ice bath, and the solution turns pink; adding additional ethyl chloroformate (0.34 mL, 3.47 mmol), and the solution gradually turns milky white; stirring for about 20 min, spotting samples onto the plate and almost no OAA-02 spot was found; adding dropwise hydroxylamine hydrochloride dissolved with methanol (0.24 g, 3.47 mmol), removing the ice bath, reacting at room temperature for 16 h, the pH of the solution was measured to be 1. By adding additional TEA (0.5 mL, 3.5 mmol), the solution turns pink and the pH is about 6. Continue to react at room temperature for 10 h, the solution becomes lighter in color; adding additional 0.5 mL of TEA, stopping the reaction after 12 h, and the solution was pink; performing suction filtration, evaporating the filtrate to dryness to obtain a residue; dissolving the residue completely with 50 mL of dichloromethane and transferring to a separatory funnel, performing extraction with 20 mL of 10% hydrochloric acid and 30 mL of distilled water, and the solution immediately became milky white turbid substances; adding additional 200 mL of dichloromethane, washing with distilled water to neutralize, and washing once with saturated brine, the solution became clear, and then drying the dichloromethane layer with anhydrous sodium sulfate; mixing the aqueous layer and performing extraction with 100 mL of dichloromethane, washing the dichloromethane with distilled water to neutralize, and washing once with saturated brine, and then drying the dichloromethane layer with anhydrous sodium sulfate; performing suction filtration on the two batches of the dichloromethane layers, and evaporating the filtrate to dryness to obtain 0.4 g; performing the column chromatographic separation (CH$_3$OH:DCM=1:50) to obtain 70 mg of pink solids, with a yield of 17%. m.p. is 296-299° C. (turns yellow at 243° C.). LC-MS (EST) m/z: 472.2 [M–H]$^-$. $^1$H-NMR. (300 MHz, DMSO-d$_6$): δ(ppm) 9.25 (1H, s, Ar—NH—CO—), 8.15-8.12 (2H, d, J=8.1 Hz), 7.91-7.88 (2H, d, J=8.7 Hz), 7.35 (1H, s, Ar—H), 1.69-1.40 (8H, m, 4×CH$_2$), 1.40 (6H, s, 2×CH$_3$), 1.30 (6H, s, 2×CH$_3$), 1.25 (6H, s, 2×CH$_3$), 1.11 (6H, s, 2×CH$_3$).

Embodiment 7

Preparation of N-(2-aminophenyl)-4-[(1,1,4,4,5,5,8,8-octamethyl-1,2,3,4,5,6,7,8-octahydro-9-anthryl) carbamoyl] benzamide (OAA-04)

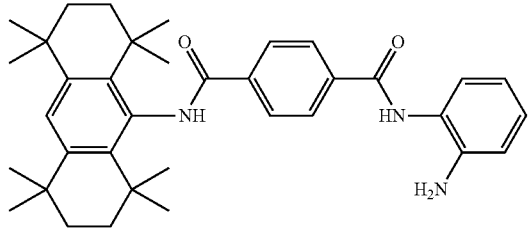 [SMILES: CC1(C)CCC(C)(C)c2c1cc1c(c2NC(=O)c2ccc(C(=O)Nc3ccccc3N)cc2)C(C)(C)CCC1(C)C]

Placing OAA-02 (0.5 g, 1.084 mmol) in a 100 mL single-mouth flask, adding 20 mL of thionyl chloride and 30 mL of dried dichloromethane, and refluxed reacting for 3 h, evaporating the solvent under atmospheric pressure to obtain 0.54 g of yellowish solids, with a yield of 96%.

Adding the above yellowish solids (0.15 g, 0.313 mmol) to a 50 mL single-mouth flask, adding 30 mL of dried 1,2-dichloroethane to dissolve the yellowish solids, stirring and adding 0.5 mL of dried triethylamine; after stirring for 10 min, adding O-phenylenediamine (0.07 g, 0.647 mmol), raising the temperature gradually and refluxed reacting under argon gas protection, the solution gradually became clear, and stopping the reaction after 9 h; Pouring the reaction solution into a separatory funnel and washing for three times with saturated brine, then drying the organic layer with anhydrous sodium sulfate overnight, performing suction filtration, and evaporating the filtrate to dryness to obtain 0.13 g; performing the column chromatographic separation (eluent PE:EA=4:1—DCM:CH$_3$OH=100:1) to obtain 0.01 g of white solids, with a yield of 6%. m.p. is higher than 300° C. (turns yellow at 270° C.), LC-MS (ESI) m/z: 552.3 [M+H]$^+$, 574.2 [M+Na]$^+$, 590.2 [M+K]$^+$, 550.1 [M–H]$^-$, 586.1 [M+Cl]$^-$. $^1$H-NMR (600 MHz, DMSO-d$_6$): δ(ppm) 9.76 (1H, s, —CO—<u>NH</u>—Ar—NH$_2$), 9.30-9.25 (1H, d, Ar—NH—CO—), 8.23-8.21 (2H, d, 2Ar—H), 8.14-8.11 (2H, m, 2Ar—H), 7.37 (1H, s, Ar—H), 7.21-7.20 (1H, m, <u>H</u>—Ar—NH$_2$), 7.01-6.99 (1H, <u>H</u>—Ar—NH$_2$), 6.81-6.79 (1H, m, <u>H</u>—Ar—NH$_2$), 6.63-6.61 (1H, m, <u>H</u>—Ar—NH$_2$), 4.98 (2H, s, Ar—<u>NH$_2$</u>), 1.71-1.11 (32H, m, 4×CH$_2$, 8×CH$_3$).

The following compounds were synthesized in a similar method:

Embodiment 8

N-(2-hydroxyphenyl)-4[(1,1,4,4,5,5,8,8-octamethyl-1,2,3,4,5,6,7,8-octahydro-9-anthryl) carbamoyl] benzamide (OAA-12)

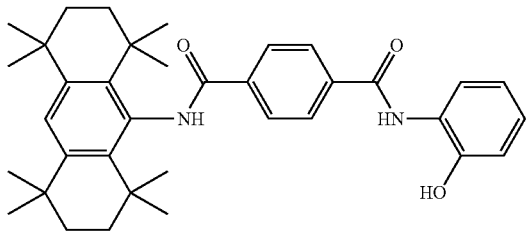 [SMILES: CC1(C)CCC(C)(C)c2c1cc1c(c2NC(=O)c2ccc(C(=O)Nc3ccccc3O)cc2)C(C)(C)CCC1(C)C]

Performing the column chromatographic separation (DCM:CH$_3$OH=300:1) to obtain 0.02 g of yellowish solids, with a yield of 7%.

m.p. is 292-294° C. (turns yellow at 287° C.), LC-MS (ESI) m/z: 552.3 [M+H]$^+$, 575.2 [M+Na]$^+$, 551.1 [M−H]$^−$. $^1$H-NMR (600 MHz, DMSO-d$_6$): δ(ppm) 9.75 (1H, s, —CO—NH—Ar—OH), 9.65-9.64 (1H, d, –OH), 9.32-9.27 (1H, d, Ar—NH—CO—), 8.23-8.11 (2H, d, 2Ar—H), 8.13-8.09 (2H, m, 2Ar—H), 7.69-7.67 (1H, m, H—Ar—OH), 7.37 (1H, s, Ar—H), 7.08-7.05 (1H, m, H—AR—OH), 6.95-6.94 (1H, m, H—Ar—OH), 6.87-6.84 (1H, m, H—Ar—OH), 1.71-1.11 (32H, m, 4×CH$_2$, 8×CH$_3$).

Embodiment 9

Preparation of N-[2-(N,N-diethylamino)]ethyl-4-[(1,1,4,4,5,5,8,8-octamethyl-1,2,3,4,5,6,7,8-octahydro-9-anthryl) carbamoyl] benzamide (OAA-05)

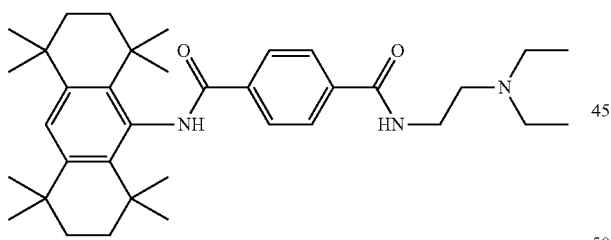

Adding the acyl chloride (0.24 g, 0.5 mmol) in the preparation of OAA-04 to a 100 mL single-mouth flask, dissolving with 30 mL DCM (not fully dissolved), and adding 1.0 mL TEA by pipette (white smoke generation, not fully dissolved); after stirring for 10 min, adding N,N-diethylethylenediamine (0.15 mL, 1.0 mmol), the solution gradually became clear, reacting at 40° C. under a condition of Ar gas protection, and stopping the reaction after 12 h; pouring the reaction solution into a 125 mL separatory funnel, washing once with 5 mL of 5% NaOH aqueous solution and washing for three times with saturated brine (insoluble substances distributed in aqueous layer), then drying the organic layer with anhydrous sodium sulfate, performing suction filtration, and evaporating the filtrate to dryness to obtain 0.17 g solids; performing column chromatography separation (PE:TEA=1000:1 for moistening the column, the eluent is DCM:CH$_3$OH=60:1) on the above solids to obtain 0.04 g of white solids, with a yield of 14%. m.p. is 272-274° C. (turns yellow at 265° C.). LC-MS (ESI) m/z: 560.42 [M+H]$^+$. $^1$H-NMR (300 MHz, CDCl$_3$): δ(ppm) 8.02-7.92 (4H, m, —CO—Ar—4H), 7.53 (1H, s, Ar—NH—CO—), 7.34 (1H, s, Ar—H), 7.1 (1H, s, —CO—NH—CH$_2$—), 3.54-3.52 (2H, m, —CO—NH—CH$_2$—), 2.70-2.68 (2H, m, —NH—CH$_2$-CH$_2$—), 2.65-2.57 (4H, q, J=6.9 Hz, 2-CH$_2$—CH$_3$), 1.85-1.2.4 (32H, m, 4×CH$_2$, 8×CH$_3$), 1.10-1.05 (6H, t, J=6.9 Hz, 2×CH$_2$CH$_3$).

The following compounds were synthesized in a similar method:

Embodiment 10

N-(2-amino) ethyl-4-[(1,1,4,4,5,5,8,8-octamethyl-1,2,3,4,5,6,7,8-octahydro-9-anthryl) carbamoyl] benzamide (OAA-06)

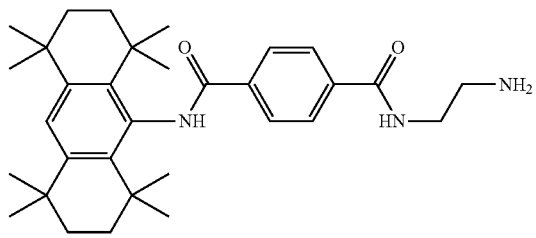 [SMILES: CC1(C)CCC(C)(C)c2c1cc1c(c2NC(=O)c2ccc(C(=O)NCCN)cc2)C(C)(C)CCC1(C)C]

Performing the column chromatographic separation (PE:TEA=1000:1 for moistening the column, the eluent is DCM:CH$_3$OH=20:1) to obtain 0.05 g of white solids, with a yield of 20%. m.p. is 268-273° C. (turns yellow at 221° C.). LC-MS (ESI) m/z: 504.3 [M+H]$^+$. $^1$H-NMR (600 MHz, CDCl$_3$)): δ(ppm) 7.96-7.94 (4H, m, —CO—AR—4H), 7.69 (1H, s, Ar—NH—CO—), 7.43 (1H, s. Ar—H), 7.1-7.06 (1H, t, —CO—NH—CH$_2$—), 3.53-3.51 (2H, m, —CO—NH—CH$_2$—), 2.96-2.93 (2H, m, —NH—CH$_2$-CH$_2$—), 1.817 (2H, s, —NH$_2$), 1.80-1.21 (32H, m, 4×CH$_2$, 8×CH$_3$).

Embodiment 11

N-[2-(N,N-dimethylamino)]ethyl-4-[(1,1,4,4,5,5,8,8-octamethyl-1,2,3,4,5,6,7,8-octahydro-9-anthryl) carbamoyl] benzamide (OAA-07)

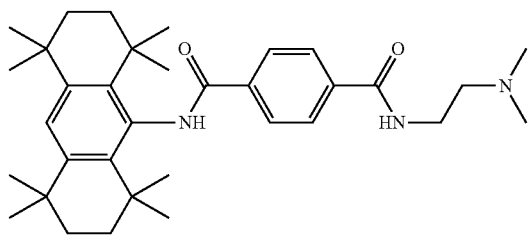

Performing the column chromatographic separation (PE:TEA=1000:1 for moistening the column, the eluent is DCM:CH$_3$OH=60:1) to obtain 0.06 g of white solids, with a yield of 22%. m.p. is 269-273° C. (turn yellow at 264° C.). LC-MS (ESI) m/z: 532.3 [M+H]$^+$. $^1$H-NMR. (600 MHz, CDCl$_3$): δ(ppm) 8.02-7.94 (4H, m, —CO—AR—4H), 7.54 (1H, s, Ar—NH—CO—), 7.35 (1H, s, Ar—H) 6.98 (1H, s, —CO—NH—CH$_2$—), 3.57-3.54 (2H, q, J=5.4, —CO—

NH—CH$_2$—), 2.57-2.55 (2H, t, J=5.4, —NH—CH$_2$-CH$_2$—), 2.30 (6H, s, 2×CH$_3$), 1.82-1.24 (32H, m, 4×CH$_2$, 8×CH$_3$).

Preparation of OAB Series Compounds

Embodiment 12

Preparation of 4[(1,1,4,4,5,5,8,8-octamethyl-1,2,3,4, 5,6,7,8-octahydro-9-anthryl) carbamoyl] aniline (OAB-01)

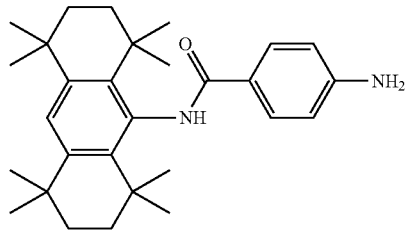 [SMILES: CC1(C)CCC(C)(C)c2c1cc1c(c2NC(=O)c2ccc(N)cc2)C(C)(C)CCC1(C)C]

Placing OA-HY (1.0 g, 3.19 mmol) in a 100 mL single-mouth flask, adding 30 mL of dried xylene to dissolve OA-HY completely, then adding DMAP (0.08 g, 0.65 mmol), dried Py (3.0 mL, 37.3 mmol), and p-nitrobenzoyl chloride (1.18 g, 6.38 mmol) successively, and refluxed reacting for 12 h under argon gas protection; reducing the temperature to 70° C. slowly, slowly dropping about 20 mL of methanol (anhydrous) to the reaction solution, then transferring to a 500 mL single-mouth flask, adding methanol (anhydrous) to about 250 mL, refluxing for 2 h, and performing immediate filtration; washing the residue with distilled water, and drying to obtain 1.27 g of amide intermediate, with a yield of 86.2%. Placing the above amide intermediate (1.0 g, 2.16 mmol) in a 250 mL single-mouth flask, adding the mixed solvent of 50 mL absolute ethanol and 130 mL tetrahydrofuran, adding 0.1 g of palladium-carbon (palladium content: 10%) without fully dissolving, performing argon gas exchange for 3 times, performing hydrogen gas exchange for 3 times, reacting at 30° C. for 25 h; Adding 50 mL of dichloromethane to the reaction solution, then stirring for 30 min, filtering through a common funnel, and evaporating the filtrate to dryness to obtain 0.9 g white powder, with a yield of 96%. m.p. is 308-310° C. LC-MS (EST) m/z: 433.2 [M+H]$^{30}$, 455.2 [M+Na]$^+$, 471.1 [M+K]$^+$. $^1$H-NMR (300 MHz, CDCl$_3$): δ(ppm) 7.76-7.73 (2H, d, J=8.7 Hz), 7.30 (1H, s, Ar—H), 7.27 (1H, s, —NH—CO—), 6.72-6.70 (2H, d, J=8.4 Hz), 1.84-1.19 (32H, m, 4×CH$_2$, 8×CH$_3$).

Embodiment 13

Preparation of 4-[(1,1,4,4,5,5,8,8-octamethyl-1,2,3, 4,5,6,7,8-octahydro-9-anthryl) carbamoyl] ethyl phenylcarbamate (OAB-02)

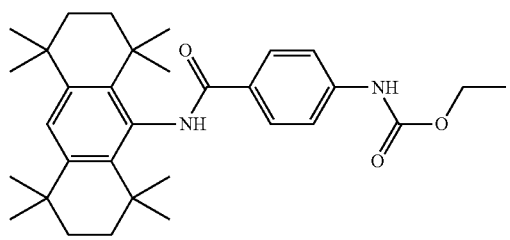 [SMILES: CCOC(=O)Nc1ccc(C(=O)Nc2c3c(cc4c2C(C)(C)CCC4(C)C)C(C)(C)CCC3(C)C)cc1]

Placing OAB-01 (0.22 g, 0.5 mmol) in a 100 mL single-mouth flask, adding 50 mL of dried THF, not fully dissolved, then adding TEA (0.2 mL, 1.43 mmol), ethyl chloroformate (0.1 mL, 1.0 mmol) successively, reacting at room temperature for 2.5 h, and reacting at 40° C. for 17.5 h; adding additional 0.2 mL TEA, 0.15 mL ethyl chloroformate, reacting at 40° C. for 5.5 h, reacting at 60° C. for 19 h, adding 0.2 mL of ethyl chloroformate, and after reacting at 60° C. for 3 h, the reaction is almost completed. Stopping the reaction, performing suction filtration, evaporating the filtrate to dryness, and dissolving it with about 200 mL of DCM completely, then washing twice with distilled water, washing once with saturated brine, drying with anhydrous sodium sulfate, and performing suction filtration; evaporating the filtrate to dryness to obtain 0.17 g yellowish solids, with a yield of 67%. m.p. is 277-279° C. (turns yellow at 237° C.), LC-MS (ESI) m/z: 505.34 [M+H]$^+$. $^1$H-NMR (300 MHz, CDCl$_3$): δ(ppm) 7.91-7.87 (2H, d, J=8.7 Hz), 7.53-7.50 (2H, d, J=8.7 Hz), 7.40 (1H, s, —NH—CO—), 7.32 (1H, s, Ar—H), 6.76 (1H, s, —NH—CO—O—), 3.30-3.23 (2H, —OCH$_2$—) 1.84-1.19 (32H, m, 4×CH$_2$, 8×CH$_3$), 1.14-1.08 (3H, m, —CH$_3$).

Embodiment 14

Preparation of 4-[(1,1,4,4,5,5,8,8-octamethyl-1,2,3, 4,5,6,7,8-octahydro-9-anthryl) carbamoyl] phenyl-carbamoyl-1-morpholine (OAB-03)

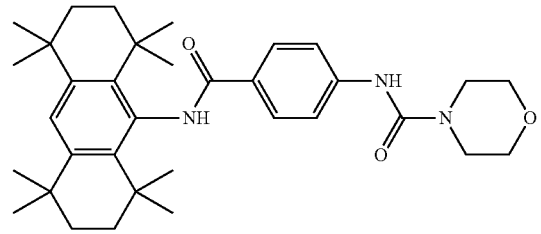 [SMILES: CC1(C)CCC(C)(C)c2c1cc1c(c2NC(=O)c2ccc(NC(=O)N3CCOCC3)cc2)C(C)(C)CCC1(C)C]

Placing OMB-01 (0.22 g, 0.5 mmol) in a 50 mL single-mouth flask, dissolving the OAB-01 completely with 25 mL of dried DCM, then adding dried. TEA (0.2 mL, 1.43 mmol), and adding BTC (0.1 g, 0.33 mmol), white smoke appeared instantly and solid is precipitated. After reacting for 1.5 h at room temperature, adding morpholine (0.1 mL, 1.14 mmol), then reacting for 3 h at room temperature, and adding 0.1 mL of morpholine; continuing the reaction at room temperature for 19 h, performing suction filtration, washing the residue with distilled water and then drying in a watch glass to obtain 0.2 g of white solids, with a yield of 73%. m.p. is 299-301° C. (turns yellow at 291° C.). LC-MS (ESI) m/z: 505.34 [M+H]$^+$. $^1$H-NMR (300 MHz, DMSO-d$_6$): δ(ppm) 8.75 (1H, s, —NH—CO—), 8.72 (1H, s, —NH—CO—N=7.98-7.95 (2H, d, J=8.4 Hz), 7.62-7.58 (2H, d, J=8.7 Hz), 7.32. (1H, s, Ar—H), 3.64-3.60 (4H, m, 2×OCH$_2$), 3.48-3.44 (4H, m, 2×NCH$_2$), 1.66-1.30 (8H, m, 4×CH$_2$), 1.40 (6H, s, 2×CH$_3$), 1.29 (6H, s, 2×CH$_3$), 1.24 (6H, s, 2×CH$_3$), 1.12 (6H, s, 2×CH$_3$).

Embodiment 15

Preparation of 1-(2-aminophenyl)-3-{4-[(1,1,4,4,5,5,8,8-octamethyl-1,2,3,4,5,6,7,8-octahydro-9-anthryl) carbamoyl] phenyl} urea (OAB-04)

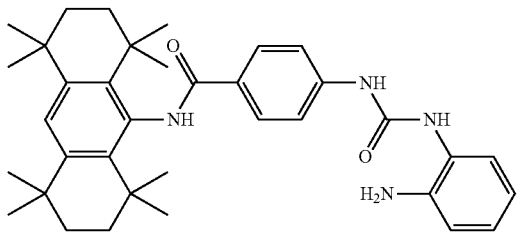 [SMILES: CC1(C)CCC(C)(C)c2c1cc1c(c2NC(=O)c2ccc(NC(=O)Nc3ccccc3N)cc2)C(C)(C)CCC1(C)C]

Placing OAB-01 (0.22 g, 0.5 mmol) in a 100 mL three-necked flask, dissolving the OAB-01 completely with 30 mL of dried DCM, adding dried TEA (0.2 mL, 1.43 mmol), then adding BTC (0.06 g, 0.2 mmol), the turbidity instantly appeared; then reacting for 30 min at room temperature, adding o-phenylenediamine (0.05 g, 0.5 mmol) to the reaction solution, reacting for 10 h at room temperature; performing suction filtration, washing the residue with distilled water for 5 times and then drying to obtain 0.12 g of pale pink solids, with a yield of 42%. m.p. is 251-257° C. (turns yellow at 231° C.). LC-MS (ESI) m/z: 567.3 [M+H]$^+$, 589 [M+Na]$^+$ 605 [M+K]$^+$, $^1$H-NMR. (600 MHz, DMSO-d$_6$): δ (ppm) 10.57 (2H, s, —NH—CO—NH—), 9.20-9.16 (1H, m, —NH$_2$), 8.9 (1H, s, —NH—CO—), 8.04-8.02 (2H, d, J=8.4 Hz), 7.97-7.93 (1H, m, —NH$_2$), 7.60-7.58 (2H, d, J=9.0 Hz), 7.38-7.37 (1H, m, H—Ar—NH$_2$), 7.34 (H, s, Ar—H), 6.89-6.86 (1H, m, H—Ar—NH$_2$), 6.78-6.76 (1H, m, H—Ar—NH$_2$), 6.63-6.60 (1H, m, H—Ar—NH$_2$), 1.72-1.49 (8H, m, 4×CH$_2$), 1.46 (6H, s, 2×CH$_3$), 1.30 (6H, s, 2×CH$_3$), 1.24 (6H, s, 2×CH$_3$), 1.11 (6H, s, 2×CH$_3$).

The Following Compounds were Synthesized in a Similar Method

Embodiment 16

1-(2-amino) ethyl-3-{4-[(1,1,4,4,5,5,8,8-octamethyl-1,2,3,4,5,6,7,8-octahydro-9-anthryl) carbamoyl] phenyl} urea (OAR-14)

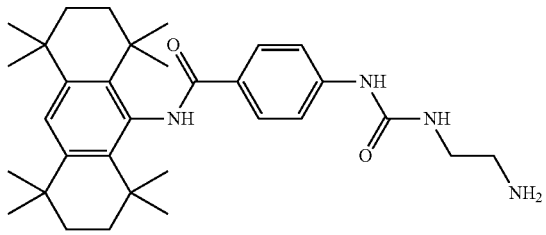 [SMILES: CC1(C)CCC(C)(C)c2c1cc1c(c2NC(=O)c2ccc(NC(=O)NCCN)cc2)C(C)(C)CCC1(C)C]

0.08 g of white solids are obtained, with a yield of 31%. m.p. is higher than 300° C. LC-MS (ESI) m/z: 519.3 [M+H]$^+$, 541.2 [M+Na]$^+$, 557.2 [M+K]$^+$. $^1$H-NMR (600 MHz, DMSO-d$_6$): δ(ppm) 8.93 (1H, s, Ar—NH—CO—NH—), 8.83 (1H, s, —NH—CO—), 7.97-7.95 (2H, d, J=8.4 Hz), 7.52-7.50 (2H, d, J=8.4 Hz), 7.32 (1H, s, Ar—H), 6.35-6.33 (1H, t, J=5.4 Hz, Ar—NH—CO—NH—), 3.11-3.08 (2H, q, J=6.0 Hz, —CO—NH—CH$_2$—), 2.64-2.62 (2H, t, J=6.0 Hz, —CH$_2$—NH$_2$), 1.70-1.40 (8H, m, 4×CH$_2$), 1.39 (6H, s, 2×CH$_3$), 1.29 (6H, s, 2/CH$_3$), 1.24 (6H, s, 2×CH$_3$), 1.09 (6H, s, 2/CH$_3$).

Embodiment 17

1-(2-hydroxy) ethyl-3-{4-[(1,1,4,4,5,5,8,8-octamethyl-1,2,3,4,5,6,7,8-octahydro-9-anthryl) carbamoyl] phenyl} urea (OAB-17)

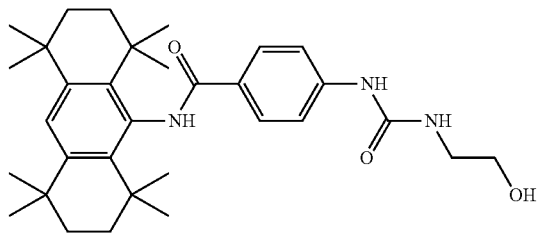 [SMILES: CC1(C)CCC(C)(C)c2c1cc1c(c2NC(=O)c2ccc(NC(=O)NCCO)cc2)C(C)(C)CCC1(C)C]

0.13 g of white solids are obtained, with a yield of 50%. m.p. is 284-287° C. (turns yellow at 278° C.). LC-MS (ESI) m/z: 520.3 [M+H]$^+$, 542.2 [M+Na]$^+$, 564.3 [M+HCOO]$^-$. $^1$H-NMR (600 MHz, DMSO-d$_6$): δ(ppm) 8.90 (1H, s, Ar—NH—CO—NH—), 8.85 (1H, s, —NH—CO—), 7.98-7.96 (2H, d, J=8.4 Hz), 7.52-7.50 (2H, d, J=9.0 Hz), 7.33 (1H, s, Ar—H), 6.32-6.30 (1H, t, J=5.4 Hz, Ar—NH—CO—NH—), 4.78-4.76 (1H, t, J=5.4 Hz, —OH), 3.47-3.44 (2H, q, J=5.4 Hz, —CO—NH—CH$_2$—), 3.19-3.16 (2H, q, J=5.4 Hz, —CH$_2$—OH), 1.70-1.41 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, ×2×CH$_3$).

Embodiment 18

1-(3-hydroxy) propyl-3-{4-[(1,1,4,4,5,5,8,8-octamethyl-1,2,3,4,5,6,7,8-octahydro-9-anthryl) carbamoyl] phenyl} urea (OAB-18)

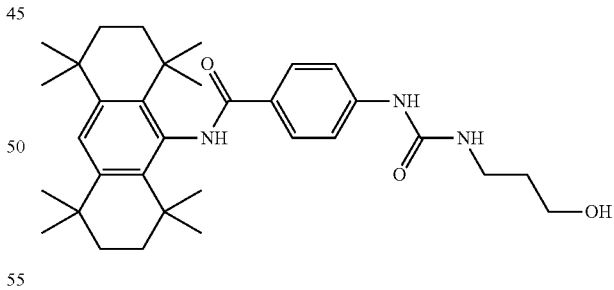

0.16 g of white solids are obtained, with a yield of 60%. m.p. is 280-282° C. LC-MS (ESI) m/z: 520.3 [M+H]$^+$, 542.2 [M+Na]$^+$, 564.3 [M+HCOO]$^-$. $^1$H-NMR (600 MHz, DMSO-d$_6$): δ(ppm) 8.84 (1H, s, —NH—CO—), 8.80 (1H, s, Ar—NH—CO—NH—), 7.98-7.96 (2H, d, J=8.4 Hz), 7.52-7.50 (2H, d, J=8.4 Hz), 7.33 (1H, s, Ar—H), 6.27-6.25 (1H, t, J=5.4 HZ, Ar—NH—CO—NH—), 4.53-4.51 (1H, t, J=4.8 Hz, —OH), 3.48-3.45 (2H, q J=5.4 Hz, —CO—NH—CH$_2$—), 3.18-3.15 (2H, q, J=6.6 Hz, —CH$_2$—OH), 1.70-1.40 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, 2×CH$_3$), 1.61-1.57 (2H, m, —CH$_2$—CH$_2$—CH$_2$—).

Embodiment 19

Preparation of N,N-dimethylsulfonyl-4-[(1,1,4,4,5,5,8,8-octamethyl-1,2,3,4,5,6,7,8-octahydro-9-anthryl) carbamoyl] aniline (OAB-05)

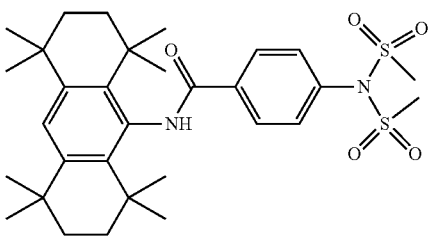 [SMILES: CC1(C)CCC(C)(C)c2c1cc1c(c2NC(=O)c2ccc(N(S(C)(=O)=O)S(C)(=O)=O)cc2)C(C)(C)CCC1(C)C]

Placing OAB-01 (0.22 g, 0.5 mmol) in a 50 mL three-necked flask, dissolving the OAB-01 completely with 30 mL of dried DCM, adding dried TEA (0.2 mL, 1.43 mmol), slowly dropping methanesulfonyl chloride (0.1 mL, 1.25 mmol) under the condition of ice bath (2-3° C.), and the reaction completed after 0.5 h; pouring the reaction solution into a 125 mL separatory funnel, washing with 5% hydrochloric acid (10 mL×1), and washing with saturated brine (15 mL×3); then drying the DCM layer with anhydrous sodium sulfate for 3 h, performing suction filtration, and evaporating the filtrate to dryness to obtain 0.16 g yellowish solids, with a yield of 54%. m.p. is 283-286° C. LC-MS (ESI) m/z: 589.2 [M+H]$^+$, 611 [M+Na]$^+$, 627.1 [M+K]$^+$. $^1$H-NMR (600 MHz, CDCl$_3$): δ(ppm) 8.05-8.03 (2H, d, J=8.4 Hz), 7.53-7.51 (2H, d, J=8.4 Hz), 7.51 (1H, s, —NH—CO—), 7.35 (1H, s, Ar—H), 3.44 (6H, s, 2×CH$_3$), 1.82-1.42 (8H, m, 4×CH$_2$), 1.41 (6H, s, 2×CH$_3$), 1.30 (6H, s, 2×CH$_3$), 1.24 (6H, s, 2×CH$_3$), 1.23 (6H, s, 2×CH$_3$).

Embodiment 20

Preparation of 1-(4-carboxypropyl)-3-{4-[(1,1,4,4,5,5,8,8-octamethyl-1,2,3,4,5,6,7,8-octahydro-9-anthryl) carbamoyl] phenyl} urea (OAB-07)

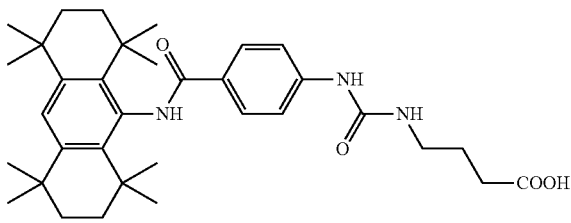 [SMILES: CC1(C)CCC(C)(C)c2c1cc1c(c2NC(=O)c2ccc(NC(=O)NCCCC(=O)O)cc2)C(C)(C)CCC1(C)C]

Placing OAB-01 (0.22 g, 0.5 mmol) in a 100 mL three-necked flask, dissolving the OAB-01 completely with 30 mL of dried DCM, adding dried TEA (0.2 mL, 1.43 mmol), then adding BTC (0.05 g, 0.17 mmol), the turbidity instantly appeared; then reacting for 30 min at room temperature, adding 4-aminobutyric acid (0.05 g, 0.5 mmol) to the reaction solution, and continuing the reaction at room temperature for 27 h, performing suction filtration, washing the residue for five times with distilled water, and then drying to obtain 0.06 g white powder, with a yield of 21%. m.p. is 277-280° C. (turns yellow at 252° C.). LC-MS (ESI) m/z: 562.3 [M+H]$^+$, 584.2 [M+Na]$^+$, 600.2 [M+K]$^+$, 560.1 [M−H]$^+$. $^1$H-NMR (600 MHz, DMSO-d$_6$): δ(ppm) 9.11 (1H, s, Ar—NH—CO—NH—), 8.84 (1H, s, Ar—NH—CO—), 7.98-7.96 (2H, d, J=8.4 Hz), 7.55-7.53 (2H, d, J=8.4 Hz), 7.34 (1H, s, Ar—H), 6.68 (1H, s, Ar—NH—CO—NH—), 3.61 (w, —COOH), 3.12-2.23 (6H, m, —CH$_2$—CH$_2$—CH$_2$—), 1.80-1.40 (8H, m, 4×CH$_2$), 1.39 (6H, s, 2×CH$_3$), 1.29 (6H, s, 2×CH$_3$), 1.24 s, 2×CH$_3$), 1.10 (6H, s, 2×CH$_3$).

Embodiment 21

Synthesis of N-{4-[(1,1,4,4,5,5,8,8-octamethyl-1,2,3,4,5,6,7,8-octahydro-9-anthryl) carbamoyl] phenylcarbamoyl}-4-piperidinyl Formic Acid (OAB-09) in a Similar Method

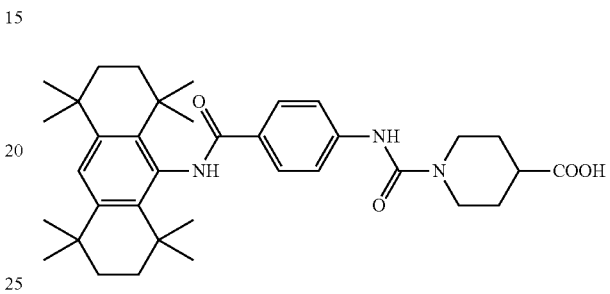

0.21 g of white solids are obtained, with a yield of 71%. m.p. is higher than 300° C. (turns yellow at 283° C.). LC-MS (ESI) m/z: 588.3 [M+H]$^+$, 610.3 [M+Na]$^-$. $^1$H-NMR (600 MHz, DMSO-d$_6$): δ(ppm) 8.86 (114, s, Ar—NH—CO—N=), 8.80 (1H, s, Ar—NH—CO—), 7.98-7.96 (2H, d, J=8.4 Hz), 7.60-7.59 (2H, d, J=8.4 Hz), 7.33 (1H, s, Ar—H), 4.05-4.02. (2H, m, —CO—N=CH$_2$), 2.96-2.92 (2H, m, —CO—N=CH$_2$), 1.86-1.84 (2H, m, =N—CH$_2$-CH$_2$—), 1.50-1.46 (2H, m, =N—CH$_2$-CH$_2$—), 1.71-1.40 (8H, m, 4×CH$_2$), 1.39 (6H, s, 2×CH$_3$), 1.29 (6H, s, 2×CH$_3$), 1.24 (6H, s, 2×CH$_2$), 1.10 (6H, s, 2×CH$_3$).

Embodiments 22 and 23

Preparation of 4-[(1,1,4,4,5,5,8,8-octamethyl-1,2,3,4,5,6,7,8-octahydro-9-anthryl) carbamoyl] methyl Phenylcarbamate (OAB-08) and 1-(2-hydroxyphenyl)-3-{4-[(1,1,4,4,5, 5,8,8-octamethyl-1,2,3,4,5,6,7,8-octahydro-9-anthryl) carbamoyl] phenyl} urea (OAB-10)

Placing OAB-01 (0.22 g, 0.5 mmol) in a 100 mL three-necked flask, dissolving the OAB-01 completely with 30 mL of dried DCM, adding dried TEA (0.2 mL, 1.43 mmol), then adding BTC (0.05 g, 0.17 mmol), the turbidity instantly appeared; after reacting for 30 min at room temperature, 0.2 g of white solids were obtained by suction filtration.

Preparation of OAB-08

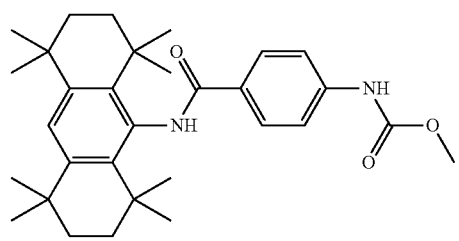

Placing the above white solids (0.1 g, 0.22 mmol) in a 50 mL single-mouth flask, adding 20 mL of methanol (anhydrous); refluxing for 3 h to obtain 0.08 g of white powder, with a yield of 74%. m.p. is 277-281° C. (turns yellow at 254° C.), LC-MS (ESI) m/z: 491.3 [M+H]$^+$, 513 [M+Na]$^+$, 529.2 [M+K]$^+$. $^1$H-NMR (600 MHz, CDCl$_3$): δ(ppm) 7.92-7.90 (2H, d, J=8.4 Hz), 7.55-7.53 (2H, d, J=7.8 Hz), 7.43 (1H, s, —NH—CO—), 7.33 (1H, s, Ar—H), 6.81 (1H, s, Ar—NH—CO—O—), 3.81 (3H, s, —CH$_3$), 1.90-1.40 (8H, m, 4×CH$_2$), 1.39 (6H, s, 2×CH$_3$), 1.29 (6H, s, 2×CH$_3$), 1.24 (6H, s, 2×CH$_3$), 1.23 (6H, s, 2×CH$_3$).

Preparation of OAB-10

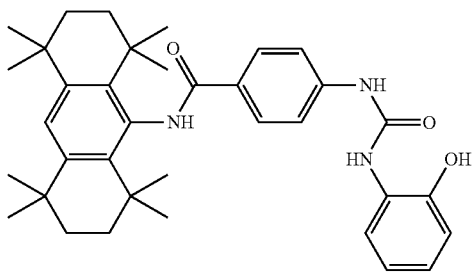 [SMILES: CC1(C)CCC(C)(C)c2c1cc1c(c2NC(=O)c2ccc(NC(=O)Nc3ccccc3O)cc2)C(C)(C)CCC1(C)C]

Placing the above white solids (0.1 g, 0.22 mmol) in a 100 mL single-mouth flask, adding 50 mL of dried DCM, then adding o-aminophenol (0.025 g, 0.23 mmol), and reacting at room temperature for 30 h; then, performing suction filtration, washing the residue five times with distilled water, and drying to obtain 0.05 g pale pink powder, with a yield of 74%. m.p. is higher than s300° C. LC-MS (ESI) m/z: 568.3 [M+H]$^+$, 590.2 [M+Na]$^+$, 606.2 [M+K]$^+$, 566.2 [M–H]$^-$, 602 [M+Cl]$^-$. $^1$H-NMR (600 MHz, DMSO-d$_6$): δ(ppm) 9.97 (1H, s, —OH), 9.63 (1H, s, —NH—CO—NH—), 8.9 (1H, s, —NH—CO—), 8.26 (1H, s, —NH—CO—NH—), 8.06-8.05 (1H, m, H—Ar—OH), 8.04-8.02 (2H, d, J=7.8 Hz), 7.60-7.58 (2H, d, J=8.4 Hz), 7.33 (1H, s, Ar—H), 6.86-6.74 (3H, m, 3H—Ar—OH), 1.71-1.40 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, 2×CH$_3$).

Embodiment 24

Preparation of 1-[2-(N,N-diethylamino)]ethyl-3-{4-[(1,1,4,4,5,5,8,8-octamethyl-1,2,3,4,5,6, 7,8-octahydro-9-anthryl) carbamoyl] phenyl} urea (OAB-12)

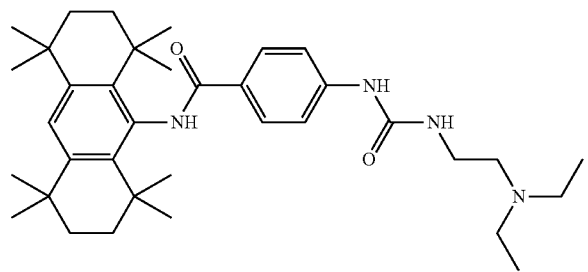 [SMILES: CCN(CC)CCNC(=O)Nc1ccc(C(=O)Nc2c3c(cc4c2C(C)(C)CCC4(C)C)C(C)(C)CCC3(C)C)cc1]

Placing OAB-01 (0.11 g, 0.25 mmol) in a 50 mL three-necked flask, dissolving the OAB-01 completely with 15 mL of dried DCM, adding dried TEA (0.15 mL, 1.07 mmol), stirring for 5 min, then adding BTC (0.03 g, 0.1 mmol), the turbidity instantly appeared; then reacting for 30 min at room temperature, slowly dropping N,N-diethylethylenediamine (0.1 mL, 0.75 mmol) with pipette into the reaction solution, and the solution gradually became clear; continuing the reaction at room temperature for 20 h, pouring the reaction solutions into a separatory funnel, adding a portion of DCM, and successively washing with 5% hydrochloric acid (5 mL×1), distilled water (30 mL×2), and saturated brine (10 mL×1) to neutralize; drying with sodium sulfate for 3 h, performing suction filtration, and evaporating the filtrate to dryness to obtain 0.16 g yellowish solids; performing column chromatography separating (eluent is EA—CH$_3$OH: DCM=2.5:1) on the yellowish solids to obtain 0.05 g of white solids, with a yield of 35%. m.p. is 286-289° C. (turns yellow at 261° C.). LC-MS (ESI) m/z: 575.3 [M+H]$^+$, 573.3 [M–H]$^-$, 609.2 [M+Cl]$^-$, 619.3 [M+HCOO]$^-$. $^1$H-NMR (600 MHz, DMSO-d$_6$): δ(ppm) 9.01 (1H, s, Ar—NH—CO—NH—), 8.84 (1H, s, —NH—CO—), 7.98-7.96 (2H, d, J=8.4 Hz), 7.52-7.50 (2H, d, J=8.4 Hz), 7.33 (1H, s, Ar—H), 6.16-6.14 (1H, t, J=5.4 Hz, Ar—NH—CO—NH—), 3.17-3.14 (2H, q, J=6.0 Hz, —CO—NH—CH$_2$—), 2.48-2.46 (2H, t, J=6.0 Hz, —CH$_2$—N=), 1.71-1.40 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, 2×CH$_3$), 1.0-0.9 (6H, t, 2×CH$_2$CH$_3$).

Embodiment 25

Preparation of 1-[2-(N,N-dimethylamino)]ethyl-3-{4-[(1,1,4,4,5,5,8,8-octamethyl-1,2,3,4,5, 6,7,8-octahydro-9-anthryl) carbamoyl] phenyl} urea (OAB-13) in a similar method

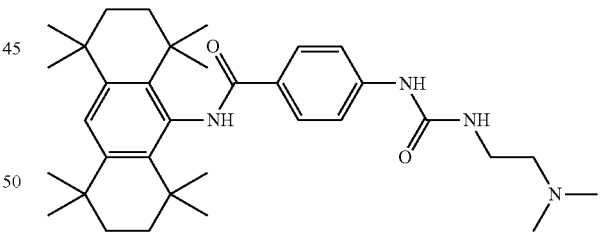

Performing the column chromatography separation (eluent is EA—CH$_3$OH:DCM=2.5:1) to obtain 0.06 g of white solids, with a yield of 44%. m.p. is 297-301° C. (turns yellow at 291° C.). LC-MS (EST) m/z: 547.4 [M+H]$^+$, 545.2 [M–H]$^-$, 581.2 [M+Cl]$^+$. $^1$H-NMR (600 MHz, DMSO-d$_6$): δ(ppm) 8.98 (1H, s, Ar—NH—CO—NH—), 8.83 (1H, s, —NH—CO—), 7.97-7.95 (2H, d, J=8.4 HZ), 7.51-7.49 (2H, d, J=8.4 Hz), 7.33 (1H, s, Ar—H), 6.21-6.20 (1H, t, J=5.4 Hz, Ar—NH—CO—NH—), 3.21-3.18 (2H, q, J=5.4 Hz, —CO—NH—CH$_2$—), 2.34-2.32 (2H, J=6.0 Hz, —CH$_2$—N=), 2.18 (6H, s, 2×N=CH$_3$), 1.70-1.40 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, 2×CH$_3$).

Embodiments 26 and 27

Preparation of 1-hydroxy-3-{4-[(1,1,4,4,5,5,8,8-octamethyl-1,2,3,4,5,6,7,8-octahydro-9-anthryl) carbamoyl] phenyl} urea (OAB-15) and 4-[(1,1,4,4,5, 5,8,8-octamethyl-1,2,3,4,5, 6,7,8-octahydro-9-anthryl) carbamoyl] phenyl Carbamic Acid-O-Amino Ester (OAB-16)

Adding OAB-01 (0.22 g, 0.5 mmol) to a 100 mL single-mouth flask, adding 50 mL of dried DCM to dissolve the OAB-01 completely (at room temperature), then adding TEA (0.2 mL, 1.43 mmol), BTC (0.06 g, 0.2 mmol) successively, and reacting for 0.5 h at room temperature; adding hydroxylamine hydrochloride (0.04 g, 0.57 mmol) to the reaction solution, and continuing the reaction at room temperature for 2 days (found unreacted), refluxed reacting for 40 h; pouring the reaction solution into a 125 mL separatory funnel, washing once with 10 mL of 1 mol/HCl aqueous solution, then washing once with distilled water, and washing with saturated brine to neutralize, drying the organic layer with anhydrous sodium sulfate, performing suction filtration, and evaporating to dryness to obtain 0.14 g of solids; performing the column chromatography separation (eluent is DCM: $CH_3OH$=60:1).

OAB-15

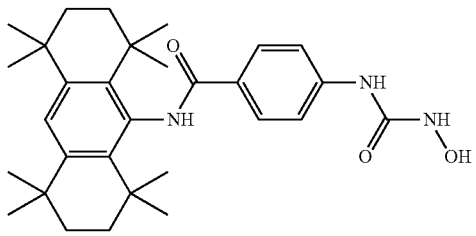 [SMILES: CC1(C)CCC(C)(C)c2c1cc1c(c2NC(=O)c2ccc(NC(=O)NO)cc2)C(C)(C)CCC1(C)C]

0.01 g light pink solids are obtained, with a yield 4%. m.p. is 290-294° C. (turns yellow at 270° C.). LC-MS (ESI) m/z: 534.3 [M+H]$^+$. $^1$H-NMR (300 MHz, DMSO-d$_6$): δ(ppm) 9.05 (2H, m, Ar—NH—CO—NH—OH), 9.00 (1H, s, Ar—NH—CO—NH—OH), 8.9 (1H, s, —NH—CO—), 8.0-7.97 (2H, d, J=8.4 Hz), 7.79-7.63 (2H, d, J=9.0 Hz), 7.33 (1H, s, Ar—H), 1.70-1.40 (8H, m, 4×CH$_2$), 1.39 (6H, s, 2×CH$_3$), 1.29 (6H, s, 2×CH$_3$), 1.24 (6H, s, 2×CH$_3$), 1.10 (6H, s, 2×CH$_3$).

OAB-16

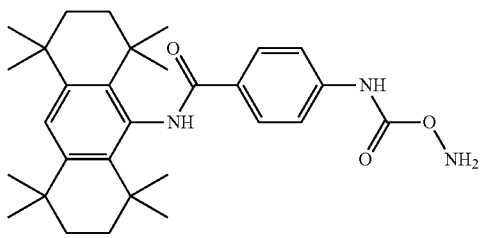 [SMILES: CC1(C)CCC(C)(C)c2c1cc1c(c2NC(=O)c2ccc(NC(=O)ON)cc2)C(C)(C)CCC1(C)C]

0.01 g of white solids are obtained, with a yield 4%. m.p. is higher than 300° C. $^1$H-NMR (300 MHz, DMSO-d$_6$): δ(ppm) 10.51 (1H, s, Ar—NH—CO—O—), 9.03 (1H, s, —NH—CO—), 8.1-8.07 (2H, d, J=8.4 Hz), 7.79-7.76 (2H, d/=8.7 Hz), 7.35 (1H, s, Ar—H), 1.70-1.40 (8H, m, 4×CH$_2$×), 1.40 (6H, s, 2×CH$_3$), 1.30 (6H, s, 2×CH$_3$), 1.25 (6H, s, 2×CH$_3$), 1.11 (6H, s, 2×CH$_3$).

II: Biological Activity
i. Antitumor Activity Test
1.1. Experimental samples and materials:
1.1. Test Drugs
OAB-1, 2, 3, 4, 5, 7, 8, 9, 10, 12, 13, 14, 15, 16, 17 and 18, OAA-1, 2, 3, 4, 5, 6, 7 and 12.
1.2. Experiment Cell Lines and Sources

| | |
|---|---|
| Human cutaneous T-cell lymphoma Hut102 cells | purchased from ATCC |
| Human leukemia HL60 cells | purchased from ATCC |
| Human non-small cell lung cancer A549 cells | purchased from ATCC |
| Human embryonic kidney 293T cells | purchased from ATCC |

1.3. Reagents

| | |
|---|---|
| RPMI1640 medium | GIBCO Lot number: NUDO160 |
| Fetal bovine serum | TIAN JIN HAO YANG BIOLOGICAL MANUFACTURE CO., LTD Lot number: 20090525 |
| Methyl thiazol tetrazolium (MTT) | Sigma Lot number: 201108, USA |
| Dimethyl sulfoxide (DMSO) | Shenyang Chemical Reagent Factory |
| NaCl | Shenyang Chemical Reagent Factory |
| KCl | Shenyang Chemical Reagent Factory |
| KH$_2$PO$_3$ | Shenyang Chemical Reagent Factory |
| Na$_2$HPO$_3$ | Shenyang Chemical Reagent Factory |
| NaHCO$_3$ | Shenyang Chemical Reagent Factory |
| Microplate reader | TECAN, Austria |
| 96-well cell culture plate | Costar Corporation |
| Dual-Luciferase Reporter | Promega Corporation Assay System: |
| HDAC Fluorometric Activity | BioVision Corporation Assay Kit: |
| DH5α competent cells | Bioteke Corporation, Beijing, China |
| Lipofectamine ® 2000 | Invitrogen |
| Endo-free Plasmid Mini Kit | OMEGA |

2. Experiment Methods
2.1. Drug Treatment

All the compounds were prepared into mother liquors with the same concentration (100 mmol/L) and stored at a temperature of −20° C. In the experiments of inhibition of cell proliferation, the test drugs and the positive control drugs SAHA and BEXA were diluted to 10 μmol/L in RPMI1640 medium at the initial screening stage. The DMSO sample was tested at a final concentration of 1%. In the rescreening stage, the concentrations of each of the initial screened test drugs and the concentrations of each of the positive control drugs of SAHA and Bexarotene in the initial screening stage were all set to 100 μmol/L, 10 μmol/L, 1 μmol/L, and 0.1 μmol/L. In the verification experiment of HDAC target, the concentrations of the test drugs and the positive control drug SAHA were set to 20 μmol/L in the initial screening stage. In the rescreening stage, the concentrations of each of the drugs were set to 20 μmol/L, 2 μmol/L, 0.2 μmol/L, and 0.02 μmol/L. In the verification experiment of RXR target, the concentrations of the test drugs and the positive control drug BEXA were set to 20 μmol/L.

2.2, MTT Assay
1) Basic Principle of MTT Assay
The survival rate of cells was determined by MTT assay, which is based on the metabolic reduction of 3-(4,5-dimethyl-2thiahiazoyl)-3,5-di-phenyl-tetrazolium bromide (MTT) by viable cells. MTT is a yellow compound, a dye that accepts hydrogen ion, which can act on the respiratory chain in the mitochondria of viable cells. Under the action of succinate dehydrogenase and cytochrome C, the tetrazolium ring was cleaved to form blue Formazan crystals, and the amount of Formazan crystals generated was only proportional to the number of the viable cells. The enzymes disappeared in dead cells, so Formazan crystals could not be dissolved in MTT solution containing 20% sodium dodecyl sulfate (pH 4.7). The optical density (OD) value at 492 nm was measured by a microplate reader, and the OD value was proportional to the amount of Formazan crystal generated, thereby reflecting the effect of the drug on the survival rate of the cells.

2) Cell Treatment

The cells in the logarithmic growth phase were selected and adjusted to an appropriate cell density, seeded in a 96-well plate, 100 μl/well, and cultured in a 37° C., 5% $CO_2$ incubator. The cells were allowed to adhere overnight, then the culture medium was replaced and the drug was added to cultivate for 48 h. A blank control group, a drug administration group and a positive control group were set, with four repeats in each group.

3) Determination Method of MTT Assay

After 48 h of drug treatment, the cells were incubated with 0.25 mg/ml MTT at 37° C. for 3-4 h, and 100 μl of dimethyl sulfoxide (DMSO) was added to each well after aspirating the culture solution. After complete dissolution, the optical density (OD) value was measured at 492 nm using the microplate reader. Finally, the cell inhibition rate of each group was calculated by taking the blank control group OD value as 100%.

$$\text{cell inhibition rate \%} = \left(1 - \frac{\text{mean value of } OD \text{ values of drug treatment group}}{\text{mean value of } OD \text{ values of positive control group}}\right) \times 100\%$$

2.3. Verification of RXR Target

1) Experiment Principle

The plasmid transfection experiment is a method for constructing a plasmid containing a target DNA sequence by means of molecular biology or the like, introducing the plasmid into the cells to be studied by transfection and observing the biochemical index. A commonly used transfection reagent was a liposome. The liposome encapsulated the DNA to form a DNA-liposome complex, which was adsorbed to the surface of the cell membrane by electrostatic interaction and introduced into the cell by endocytosis. Inside the cell, the plasmid was replicated and expressed. A sequence for expressing a reporter gene was ligated to the plasmid for transfection, and the sequence was generally a sequence expressing Firefly luciferase (FLU) or Renilla luciferase (RLU). In this experiment, the target plasmid contained the expression sequence of FLU, and its signal intensity was used to indicate the activity of the detection index. In addition, while transfecting the target plasmid, another blank plasmid containing the RLU sequence was transfected, and the signal intensity thereof was used as an internal reference to normalize the experimental results. The final results of the experiment were tested using a dual-luciferase reporter assay kit.

2) Cell Treatment a) One day before transfection, digesting 293T cells by trypsin and count, seeding the cells in 96-well plates (0.1-1×10$^5$ cells per well) and adding 100 μL of serum-containing and antibiotic-free medium to each well, the cells were able to achieve 90-95% confluence on the day of transfection.

b) Adding 0.2 μg DNA diluted by 25 μL, serum-free medium such as OPTI-MEM to each well of the cells, and mixing gently.

c) Lightly and uniformly mixing Lipofectamine 2000 transfection reagent before use; adding 0.5 μL Lipofectamine 2000 transfection reagent diluted by 25 μL serum-free OPTI-MEM to each well of the cells; mixing gently and incubating for 5 min at room temperature.

d) Mixing the diluted DNA and the diluted Lipofectamine 2000, the total volume is 50 μL; mixing gently and keeping for 20 min at room temperature to form a DNA-Lipofectamine 2000 complex.

e) Aspirating the nutrient solution in the 96-well plate and washing twice with serum-free medium; adding 100 μL, serum-free medium.

f) Adding 50 μL liposome/DNA mixture dropwise to each well while shaking the plate, and gently mixing.

g) After transfection for 4-5 h, replacing the culture medium with a serum-containing medium; adding drug and making the final concentration of the drug as 20 nM; detecting after 48 h.

3) Detection Method

Preparing the required passive lysate buffer (PLB), Stop & Glo® Reagent according to the specification of the dual-luciferase reporter assay kit. Removing the cell culture medium and washing the cells with PBS; adding 100 μL of PLB to each well, and gently shaking the cell plate for 15 min at room temperature; transferring the lysate buffer to a centrifuge tube; centrifuging the centrifuge tube at 12000 rpm for 10 min, and taking the supernatant for detection; detecting the firefly fluorescence value $OD_{(FLU)}$ and Renilla fluorescence value $OD_{(RLU)}$ of each sample, and using $OD_{(FLU)}/OD_{(RLU)}$ as the final statistical result.

2.4. Verification of HDAC Target

1) Basic Principle

The effect of the drug on HDAC activity was examined using the HDAC activity assay kit. A substrate containing an acetylated lysine chain was added to the sample (cell lysate buffer), and the active HDAC in the sample deacetylated the lysine chain on the substrate to activate the substrate. Further, a lysine luminescent reagent is added to generate fluorescence, and the signal was recorded by a microplate reader to indicate the activity of HDAC in the sample.

2) Detection Method a) Dissolving 50 μg untreated A549 cell lysate in 85 μL (final volume) dd$H_2O$. For the positive blank group, adding 2 μL HeLA nuclear extract first, following by adding 83 μL dd$H_2O$. In the negative blank group, by adding 2 μL Trichostatin A and 83 μL dd$H_2O$.

b) Adding 10 μL 10× buffer to each well.

c) Adding 5 μL HDAC fluorogenic substrate to each well, and adding the drug to make the final concentration reach the set concentration, mixing well, and incubating at 37° C. for 30 min.

d) Adding 10 μL lysine developer, mixing well, then stopping the reaction, incubating for 30 min at 37° C.

e) Detecting the fluorescence value by the microplate reader (condition: emission wavelength/excitation wavelength is 350-380/440-460 nm).

3. Statistical Methods

All data were analyzed by SPSS (16.0) statistical software package. Data of each group was expressed as mean value±standard error (Mean±S.E.). Overall differences were evaluated using One-Way ANOVA. Dunnett or Dunnett's T3 test was performed for comparison between groups.

4. Experimental Results 4.1. MTT Assay (1) Effect of the Compounds on Proliferation of Human Leukemia HL60 Cells The experimental results are shown in Table 1. The drugs (10 μM) were treated for 48 h. The compounds OAB-12, OAB-13 and OAA-6 significantly inhibited the proliferation of the human leukemia HL60 cells. The inhibition rates were all greater than 50%. The samples with inhibition rate greater than 50% after 48 h at 10 μM were selected for rescreening. The experimental results are shown in Table 2.

TABLE 1

Inhibitive rate (%) of compounds (10 μM) against HL60 cells (Mean ± SE)

| No. | Inhibitive rate (%) | No. | Inhibitive rate (%) | No. | Inhibitive rate (%) | No | Inhibitive rate (%) |
|---|---|---|---|---|---|---|---|
| Control | 0.00 ± 1.03 | OAB-5 | 42.31 ± 1.05 | OAB-14 | 24.27 ± 3.18 | OAA-2 | 3.06 ± 2.23 |
| SAHA | 66.86 ± 0.21** | OAB-7 | 1.76 ± 1.41 | OAB-15 | 0.59 ± 1.44 | OAA3 | 4.79 ± 6.65 |
| BEXA | 4.00 ± 1.14 | OAB-8 | 7.24 ± 4.74 | OAB-16 | 1.67 ± 3.24 | OAA-4 | 12.50 ± 1.32 |
| OAB-1 | 5.95 ± 2.98 | OAB-9 | 8.03 ± 1.07 | OAB-17 | 33.62 ± 0.7 | OAA-5 | 16.59 ± 1.43 |
| OAB-2 | 4.51 ± 1.80 | OAB-10 | 7.21 ± 0.96 | OAB-18 | 2.47 ± 2.64 | OAA-6 | 67.63 ± 0.06*** |
| OAB-3 | 1.71 ± 5.44 | OAB-12 | 76.96 ± 3.08 | OAA-1 | 8.27 ± 1.57 | OAA-7 | 10.77 ± 0.69 |
| OAB-4 | 15.45 ± 1.16 | OAB-13 | 80.98 ± 1.39 | | | | |

***$P < 0.001$ Vs Control;
**$P < 0.01$ Vs Control;
*$P < 0.05$ Vs Control.

TABLE 2

Inhibitive rate (%) of compounds against HL60 cells (Mean ± SE)

| No. | Control | 0.01(μmol/L) | 0.1(μmol/L) | 1(μmol/L) | 10(μmol/L) | $IC_{50}$(μmol/L) |
|---|---|---|---|---|---|---|
| SAHA | 0.00 ± 0.52 | 23.23 ± 1.48** | 74.97 ± 1.95*** | 74.48 ± 0.44*** | 75.46 ± 1.27*** | 0.69 ± 0.16 |
| BEXA | 0.00 ± 0.52 | 16.51 ± 1.66 | 15.14 ± 1.44 | 65.48 ± 1.72** | 80.88 ± 0.63*** | 6.31 ± 0.70 |
| OAB-12 | 0.00 ± 0.52 | 8.96 ± 1.45 | 11.79 ± 1.33* | 72.98 ± 1.31*** | 78.94 ± 0.42*** | 4.71 ± 0.67 |
| OAB-13 | 0.00 ± 0.52 | 12.60 ± 0.70** | 11.42 ± 0.88* | 53.30 ± 1.22** | 79.93 ± 0.16*** | 6.65 ± 2.93 |
| OAA-6 | 0.00 ± 0.52 | 1.20 ± 0.27 | 13.44 ± 1.50* | 76.73 ± 0.07*** | 79.74 ± 0.46*** | 5.63 ± 1.14 |

***$P < 0.001$ Vs Control;
**$P < 0.01$ Vs Control;
*$P < 0.05$ Vs Control.

(2) Effect of the Compounds on Proliferation of Human Cutaneous T-cell Lymphoma Hut102 Cells The experimental results are shown in Table 3.

TABLE 3

Inhibitive rate (%) of compounds (10 μM) against Hut102 cells (Mean ± SE)

| No. | Inhibitive rate (%) | No. | Inhibitive rate (%) | No. | Inhibitive rate (%) | No. | Inhibitive rate (%) |
|---|---|---|---|---|---|---|---|
| Control | 0.00 ± 1.03 | Control | 0.00 ± 1.03 | Control | 0.00 ± 1.03 | Control | 0.00 ± 1.03 |
| SAHA | 61.60 ± 0.46** | OAB-8 | −1.05 ± 3.08 | OAB-17 | 9.22 ± 1.29 | OAA-6 | 23.90 ± 1.03 |
| BEXA | 6.41 ± 4.10 | OAB-9 | −0.30 ± 1.13 | OAB-18 | 4.32 ± 1.29 | OAA-7 | 8.34 ± 4.37 |
| OAB-1 | 5.43 ± 2.54 | OAB-10 | 17.08 ± 0.93 | OAA-1 | 7.11 ± 1.06 | OAA-12 | 25.14 ± 0.65 |
| OAB-2 | 6.58 ± 1.51 | OAB-12 | 43.73 ± 3.98 | OAA-2 | −3.63 ± 1.07 | OAB-7 | 5.60 ± 3.00 |
| OAB-3 | −0.89 ± 3.47 | OAB-13 | 39.79 ± 0.81 | OAA3 | 11.33 ± 0.46 | OAB-16 | 8.38 ± 2.31 |
| OAB-4 | 34.00 ± 0.93 | OAB-14 | 41.18 ± 1.08 | OAA-4 | 30.31 ± 0.70** | | |
| OAB-5 | 29.06 ± 1.39** | OAB-15 | 2.30 ± 3.26 | OAA-5 | 27.69 ± 2.38 | | |

***$P < 0.001$ Vs Control;
**$P < 0.01$ Vs Control;
*$P < 0.05$ Vs Control.

4.2, Verification of RXR Target

After the transfected cells were treated for 48 h with 20 nM drugs, the transfected cells were tested according to the instructions of the dual-luciferase reporter assay kit. The experimental results in Table 4 show that there was no significant increase in RXR.

TABLE 4

Effect of the compounds (20 nM) on RXR activity of transfected 293T cells

| No. | Flu | Rlu | Flu/Rlu | Relative activity |
|---|---|---|---|---|
| CON | 79125 | 45003 | 1.75 | 1 |
| BEXA | 778647 | 85164 | 9.14 | 5.20 |
| OAB-12 | 4013 | 2686 | 1.49 | 0.85 |
| OAB-13 | 76228 | 39025 | 1.95 | 1.11 |
| CON | 32450 | 15924 | 2.04 | 1.16 |
| OAA-6 | 452598 | 174827 | 2.59 | 1.47 |

4.3. Verification of HDAC Target

The experimental results are shown in Table 5. After the total protein was extracted from the untreated cells, 20 μM drugs were administered for 48 h.

TABLE 5

Effect of the compounds on HDAC activity of A549 cells (%) (Mean)

| No. | Inhibitive rate |
|---|---|
| SAHA | 82.31 |
| OAB-12 | 4.17 |
| OAB-13 | 3.19 |
| OAA-6 | −11.07 |

5. Experimental Conclusions

The compounds OAB-12, OAB-13 and OAA-6 had significant inhibition effect on the proliferation of HL60 cells with $IC_{50}<10$ μmol/L. The compounds screened in the MTT assay had no significant effect on the activity of RXR.

ii. Therapeutic Activity Test of Neurodegenerative Diseases

A. Experiments and Experimental Methods

Aβ (6E10, Covance)

Thioflavin S (Sigma)

Anti-Iba1 (Abeam)

Immunohistochemistry kit: Beijing Zhongshan Goldenbrige Biotechnology Co., Ltd.

1. Animal Grouping and Administration 9 of 8-month-old C57 BL/6 mice were used as a blank control group, and 45 of APP/PS1 transgenic mice of the same age were randomly divided into a model group, a 100 mg/kg bexarotene group, a 50 mg/kg OAB-14 group, a 100 mg/kg OAB-14 group and a 200 mg/kg OAB-14 group, with 9 mice in each group. The drugs were administered three days after the adaptive feeding. Peanut oil was used as the solvent. The drug was intragastric administered once a day for 15 days. On the 6th to 9th day after the administration, the new object identification test was performed. On the 10th day, the Y-maze test was performed. On the 11th to 15th day, the Morris water maze test was performed to determine the improvement of learning and memory. The administration of the drugs was continued during the behavioral experiment until the animals were sacrificed (16th day).

2. Behavioral Experimental Method 2.1. New object Identification Test

The experimental device is a wooden square open field with a size of 50 cm×50 cm×15 cm. 2 days before the test, the mice were placed in the test site to adapt to the environment for 5 min, 1 mouse each time, and 2 times a day. On the day of the test, the animals were placed in the experimental device for free for 3 min to adapt to the environment. The animals were removed and two identical objects (A1, A2) were placed in a position parallel to the wall in the experimental device. The mouse was placed back to the objects at equal distance from the two identical objects on the other side of the experimental device, and the time (tA1, tA2) used to explore the two objects within 5 minutes was recorded. After 1 h, A2 was replaced with a new object (B) and the mouse was placed in the test site again, the time (tA1, tB) used to explore the two objects was recorded. After 24 h, the object B was replaced with a new object (C), and the mouse was placed in the test site again, the time (tA1, tC) used to explore the two objects was recorded. The mouse with a tip of the nose facing the object and less than 2 cm from the object or the mouse sniffing or licking the object is defined as an exploratory behavior, but climbing the object is not an exploratory behavior. After each mouse was removed from the test site, the excreta was quickly cleaned and the test site was wiped with 10% alcohol to eliminate the residual smell of the mouse. The preferential index and the discrimination index of the new objects for each group of the experimental mice were calculated separately.

The formula for calculating the preferential index is as follows:

$$\text{Preferential index (1 h)}=tB/(tA1+tB) \quad (1)$$

$$\text{Preferential index (24 h)}=tC/(tA1+tC) \quad (2)$$

The formula for determining the discrimination index is as follows:

$$\text{Discrimination index (1 h)}=(tB-tA1)/(tA1+tB) \quad (3)$$

$$\text{Discrimination index (24 h)}=(tC-tA1)/(tA1+tC) \quad (4)$$

2.2. Y-maze Test

The experimental device consists of three wooden arms with a same included angle of 120°, recorded as arm A, arm B and arm C, respectively. The size of each arm is 40×12×10 cm (length×height×width). During the test, the mouse was placed at the end of the arm A, allowed to freely enter and exit the three arms. The total number of times the mouse entered the three arms (number of arm entries, N) and the order of the arms entries within 5 minutes were recorded. After each mouse was removed from the test site, the excreta was quickly cleaned and the test site was wiped with 10% alcohol to eliminate the residual smell of the mouse. Entering the three different arms in succession is a correct successive alternation (successive alternation), the number of the correct successive alternations (number of alternation) vas recorded. The spatial working memory ability was reflected by the spontaneous alternation rate (alternation behavior, %). Calculation formula is as follows:

$$\text{Alternation behavior (\%)}=\text{number of alternation}/(N-2)\times 100\%$$

For example, the order in which the animal entered the three arms within the specified time is: ABCCBACABCAC-BACB, wherein N is 16, and the successive alternation is: ABC, CBA, BAC, CAB, BCA, ACB, BAC, $$\text{Alternation behavior (\%)}=[7/(16-2)]\times 100\%=50\%.$$

2.3, Morris Water Maze Test

The experimental device includes a black circular pool with a diameter of 100 cm and a height of 40 cm, and a white platform (safe platform) having a diameter of about 10 cm. The location of the safe platform could be moved. Morris Water Maze Video Detection and Analysis System was provided by the Institute of Materia Medica, China Academy of Medical Sciences. One day before the experiment, water was injected into the black circular pool (water temperature 22±1° C.), and white pigment was added to mix uniformly. The water surface was usually about 1 cm higher than the top of the safe platform. The pool was divided into four quadrants I, II, III and IV, and the safe platform was usually placed in the middle of the quadrant IV. The experiment was divided into two parts: (1) Oriented navigation: the animal grouping was input into a computer software in advance. The position of the safe platform was kept unchanged during the experiment. During the test, the experimental animal facing the pool wall was placed in the water from different inlets, and the computer simultaneously collected data and recorded the time to find the safe platform (escape latency). Data collection automatically stopped when the animal stayed on the safe platform for 10 s. The data acquisition time of the mouse was 60 s. If the animal could not find the safe platform within the specified time, the escape latency was recorded as 60 s. At the same time, the operator induced the animal to reach the safe platform and stay for 10 s. The animal was trained twice a day for 4 consecutive days. (2) Probe test: after the oriented navigation test is completed, the safe platform is removed and the animal was placed in the pool free to explore for 60 s. The camera system automatically recorded the time and distance of the experimental animal swimming in the quadrant of the safe platform within the specified time and the number of times passing through the location of the safe platform.

2.4. Social Interaction Experiment

The social interaction device was composed of a square box (length×width×height: 50 cm×50 cm×15 cm). The behavioral laboratory used diffuse and dim light (25 W) and tried to avoid environmental stress caused by shadows in the experimental area. Before the social interaction experiment, in order to eliminate the influence of unfamiliar environment, each mouse was placed in the experimental device alone to adapt to the environment, 10 min each day for two consecutive days. At the beginning of the test on day 3, the mouse was randomly paired with another strange partner. Two groups of experimental animals were placed in the experimental device at the same time, and the time spent by the mice in the active social interaction behavior was recorded. The test time was 10 min, including sniffing, combing, and scratching or chasing each other. However, passive contact activities (overwhelmed or being ridden by the other mouse, etc.) are not recorded in the social interaction behavior. After each test, 1% bromo geramine was used to disinfect the social interaction device.

2.5. Nesting Experiment

Each mouse was separately housed in a cage. On the first day of the test, two pieces of cotton (5 cm×5 cm) were placed in the cage. Photographed after 24 h and 48 h, evaluated on a 5-point scale: 1=no visible touch; 2=partial tear; 3=most debris, but no recognizable position; 4=recognizable position but flat; 5=almost perfect.

3. Detection of Protein Expression in Brain Tissue by Western Blotting 3.1. Materials After the behavioral experiment, the animals were anesthetized with an intraperitoneal injection of 3.5% chloral hydrate and cut off the heads quickly to take out the brains. The hippocampus and cortex of the brain were separated on ice, and then weighed and quickly frozen with liquid nitrogen, placed in a refrigerator at −80° C. for standby application.

3.2. Protein Extraction from Tissues

The tissue lysate (5 μL PMSF protease inhibitor per mL of lysate) was added to the frozen brain tissue at a ratio of 5:1 (6 mL/g tissue), and ultrasonically homogenized in an ice bath. After homogenization, the tissue homogenate was placed in crushed ice for 30 min, and then centrifuged at 12,000×g for 20 min at 4° C. The supernatant (about 200 μL) was taken and stored in a refrigerator at −80° C. for later use. A portion of the supernatant was taken for protein quantification.

3.3. Determination of Protein Concentration—BCA Assay

According to the kit instruction, BCA working reagent was prepared by mixing reagent A with reagent B at a ratio of 50:1 thoroughly. The BCA working reagent was freshly prepared for use at room temperature with a stable period of 24 h. (1) The 5 mg/mL BSA was diluted to a final concentration of 0.5 mg/mL with PBS to obtain a standard protein solution. (2) The standard protein solution was added to the wells of a 96-well plate at 0, 1, 2, 4, 8, 12, 16, 20 μL, and the solution of the wells was made up to 20 μL with standard dilution (PBS), 3 repetitions per concentration. (3) After the protein supernatant was diluted 100-fold with PBS, 20 μL of the diluted solution was added to a 96-well plate, 3 repetitions for each sample. (4) 200 μL BCA working reagent was added to the wells for test, and then the wells were placed at 37° C. for 30 min. (5) The absorbance of the protein (at a wavelength of 540 nm) was determined by a microplate reader. (6) The standard curve was made by Excel, and the concentration of the detected protein was calculated based on the standard curve.

3.4. Western Blot Analysis 3.4.1. Preparation of SDS-polyacrylamide Gel (SDS-PAGE)

| Reagent | Separation gel concentration (%) | | | | Stacking gel concentration (5%) |
|---|---|---|---|---|---|
| | 8 | 10 | 12 | 15 | |
| 30% Acrylamide | 4.0 ml | 5.0 ml | 6.0 ml | 7.5 ml | 0.4 ml |
| 1.5 mol/L Tris-Hcl pH 8.8 | 3.75 ml | 3.75 ml | 3.75 ml | 3.75 ml | 0.5 mol/LTris-Hcl pH 6.8 0.625 ml |
| 10% SDS | 150 μl | 150 μl | 150 μl | 150 μl | 25 μl |
| 10% AP | 150 μl | 150 μl | 150 μl | 150 μl | 8.3 μl |
| ddH$_2$O | 6.9 ml | 5.9 ml | 4.9 ml | 3.4 ml | 1.44 ml |
| TEMED | 8 μl | 8 μl | 8 μl | 8 μl | 2.5 μl |

The gels were made as follows:
1) Preparing 8-12% separation gel; after adding Tris-Nacl, polyacrylamide and TESTED in proportion, mixing well and pouring into the gap between the glass plates.
2) Filling the top of the separation gel with deionized water.)
3) Standing at room temperature for 30 min to promote the separation gel to polymerize.
4) After the separation gel is polymerized, pouring off and drying the deionized water, and gently sucking the residual liquid at the top of the gel by the filter paper.
5) Preparing the stacking gel according to the above ingredients and mixing well, then pouring into the gap between the glass plates, inserting the comb, sealing with Vaseline to avoid bubbles, and polymerizing at room temperature for about 50 min.
6) After the stacking gel is polymerized, removing the comb and the Vaseline, placing the stacking gel into a sealed plastic bag with deionized water and storing in the refrigerator at 4° C.

3.4.2. Electrophoresis

Electrophoretic separation was performed on the detected proteins in an 8-12% SDS-polyacrylamide gel (SDS-PAGE).
1) Denaturation: according to the results of the protein quantification by BCA assay, adjusting the protein concentrations of the samples to make the protein concentrations consistent, adding 5×SDS-PAGE loading buffer, boiling for 5 minutes at 100° C. to fully denature the proteins, and putting ice box to cool quickly for later use.
2) Preparation of electrophoresis buffer: diluting the prepared 5× electrophoresis buffer to 1× electrophoresis buffer and placing in an electrophoresis tank for later use.
3) Loading: loading the protein molecular weight standard (protein Marker) and each group of the samples, wherein 40 µg/12 µl of the detection protein was added to each well.
4) Electrophoresis: Voltage at the beginning is 80 V, after the protein Marker is separated (after forming several lines), increasing the voltage to 110 V. When the blue dye band reached the bottom of the separation gel, the electrophoresis was terminated.

3.4.3. Transfer

The proteins were transferred onto PVDF membrane by wet transfer.
1) Cutting 8 sheets of filter papers of appropriate size (determined by the number of samples) and 1 sheet of PVDF membrane, making a mark on one corner of the PVDF membrane to show the front side of the PVDF membrane.
2) Membrane activation: immersing the PVDF membrane in methanol (10-30 s), deionized water (5 min) and transfer buffer (more than 30 min) in turn.
3) Immersing PVDF membrane, the filter paper and porous filter screen in the transfer buffer for more than 30 min.
4) Preparing the blotting sandwich, from positive electrode to negative electrode, porous filter screen, filter paper, PVDF membrane, gel, (2 sheets) filter paper, porous filter screen, and black plywood box were arranged in sequence. Buckling the button of the blotting sandwich and putting the blotting sandwich into the transfer membrane tank. Placing ice boxes on both sides in the transfer membrane tank to prevent excessive heat generation during the transfer membrane process.
5) Transferring, according to the protein with negative charge, switching the current on and keeping in constant current or constant voltage. The transfer time depends on the molecular weight of the detected protein (0.5-2 h), the current is 100 mA, and the voltage is 100 V.

3.4.4. Blocking and Immune Response
1) Blocking: after the completion of the transfer, cutting the PVDF membrane into several strips according to the molecular weight, and placing the strips in 10 ml PBS milk blocking solution (Blocking buffer), and gently shaking at room temperature for 2 h.
2) Adding primary antibody: preparing the antibody with PBS milk blocking solution, incubating for 5 min at room temperature, and placing in a refrigerator at 4° C. overnight.
3) Washing the primary antibody: washing the PVDF membrane strips three times with PBS buffer at room temperature for 10 min/time on a shaker.
4) Adding secondary antibody: preparing the secondary antibody with Tris-NaCl blocking solution, uniformly adding to the PVDF membrane strips, and incubating at room temperature for 2 h.
5) Washing the second antibody: washing the PVDF membrane strips three times with Tris-NaCl buffer at room temperature for 10 min/time on a shaker.

3.4.5. Development

The immunoreactive bands were obtained by developing and fixing with SuperECL luminescent liquid.
1) Preparation before development: mixing an equal volume of luminescent liquid A and luminescent liquid B to obtain a mixed luminescent liquid. (The amount of liquid is determined according to the size of the developing membrane, and should be prepared at the time of detection).
2) Color reaction: After washing the membrane several times with the Tris-NaCl buffer, using the filter paper to remove excess luminescent liquid (avoid contact with the protein surface of the membrane), then placing the membrane on the sealed plastic bag and dripping the mixed luminescent liquid.
3) Film detection: fixing the PVDF membrane in a cassette (protein side is upward), placing the film on the PVDF membrane and exposing the film. (The exposing time varies depending on the intensity of the antibody titer)
4) Development: placing the film in the developer for 3 min, and observing the development.
5) Fixing: after development, washing the film in clean water and placing in the fixing solution for more than 5 min, and observing the expression of the target band.

3.4.6. Image Scanning and Quantitative Analysis

Grayscale scanning of the X film was performed and the results were analyzed by the image analysis software of Quantity One 4.6.2. Differences and changes in the expression of the detected proteins between the groups were determined using β-actin as an internal reference. The relative value was calculated by the formula.

Relative value=detected protein expression intensity/β-actin expression intensity 4. Immunohistochemical Staining 4.1. Material and Preparation of Tissue Samples After the behavioral experiment, the mice were anesthetized with an intraperitoneal injection of 3.5% chloral hydrate 3.5% (about 3 μl for each mouse). Then the back of the mouse was fixed on the operating table and the chest was open to expose the heart. A perfusion needle was inserted into the left ventricle from the apex of the heart, while the right atrial appendage cut a small opening. First, perfusion was performed with about 200 ml saline. When the tail of the mouse was cut to find no blood, 300 ml 4% paraformaldehyde buffer (0.1 mol/L) at 4° C. was used to perfuse until the body of the mouse was stiff. The mouse was then decapitated, and the whole brain was obtained and fixed in 4% paraformaldehyde at 4° C. After 24 h, the brain was embedded in conventional paraffin and coronally sectioned to obtain the tissue sections with a thickness of 5 μm for immunohistochemical staining.

4.2. Immunohistochemical Staining

The streptomycin avidin-peroxidase (SP) method was used for immunohistochemical detection. The biotin-labeled secondary antibody, streptomycin avidin-peroxidase and dye mixture in the SP kit were used to determine the antigen in the tissue. The specific experimental steps were as follows: tissue sections were dewaxed and taken through graded alcohols to water; microwave antigen retrieval (70% formic acid was used for antigen retrieval in Aβ6E10 staining).

Placing the tissue sections in a container containing an antigen retrieval solution, the antigen retrieval solution is a citrate buffer (0.01 M, pH 6.0), and heating to boiling in a microwave oven; after natural cooling, washing the tissue sections with the distilled water for 3 times, for 3 min each time; incubating for 10 min in 3% $H_2O_2$ at 37° C.; washing with PBS for 3 times, for 3 min each time; adding goat serum blocking solution to block for 30 min at room temperature, aspirating excess goat serum blocking solution; adding primary antibody, incubating overnight at 4° C., and in the negative control group, replacing the primary antibody with 0.01 M PBS buffer; washing with PBS for 3 times, for 5 min each time; adding biotinylated secondary antibody working solution, incubating at 37° C. for 30 min, and washing with PBS for 3 times, for 5 min each time; adding dropwise the horseradish peroxidase-labeled streptomycin avidin working solution, incubating at 37° C. for 30 min, and washing with PBS for 3 times, for 5 min each time; performing DAB development, and observing the staining intensity under a microscope to control the reaction time, when brown coloration appeared in the tissue section, washing immediately with tap water to stop dyeing; counterstaining with hematoxylin for 3 min, and washing with tap water; differentiating in hydrochloric acid alcohol for several seconds, washing fully with the tap water; dehydrating with gradient alcohol, transparentizing with xylene, and sealing with neutral gum; observing the expression of Aβ plaques in each field of the view with an optical microscope, determining the area of the Aβ plaques in each tissue section of each group of the mice by computer image analysis system.

4.3. Single-label Immunofluorescence 4.3.1. Immersing the paraffin sections in xylene to dewax for 15 min, and 2 times in total; then immersing in gradient alcohols with a gradient of 100%, 100%, 95%, 90%, 85% and 75%, each for 5 min.

4.3.2. Microwave antigen retrieval: immersing the sections in 0.01 M citrate buffer (pH 6.0), heating to boiling in a microwave oven, and repeating twice; after natural cooling, washing 2 times with PBS for 5 min each time.

4.3.3. Blocking endogenous peroxidase: blotting around the brain tissue with filter paper, outlining the brain tissue with a PAP pen. Adding dropwise the peroxidase blocker, incubating for 10 min at room temperature, and washing 3 times with PBS for 5 min each time.

4.3.4. Adding dropwise normal serum blocking solution diluted with 0.01M PBS at a ratio of 1:10, standing at room temperature for 20 min, shaking off the excess liquid and not washing.

4.3.5. Adding dropwise the primary antibody diluted with 0.01 M PBS, keeping at 4° C. overnight; washing 3 times with 0.01 M PBS for 2 min each time.

4.3.6. Adding dropwise the biotinylated secondary antibody corresponding to the primary antibody, wherein the biothinylated secondary antibody was diluted with 0.01M PBS at a ratio of 1:100, keeping at 37° C. for 30 min, and washing 3 times with PBS for 2 min each time.

4.3.7. Adding dropwise SABC-FITC (or SABC-Cy3) diluted with 0.01M PBS at a ratio of 1:100, keeping at 37° C. for 30 min, and washing 4 times with PBS for 5 min each time.

4.3.8. Sealing with water-soluble sealant; observing by fluorescence microscopy.

4.4. Double-label Immunofluorescence of Iba1 and 6E10

4.4.1 Immersing the paraffin sections in xylene to dewax for 15 min, and 2 times in total; then immersing in gradient alcohol with a gradient of 100%, 100%, 95%, 90%, 85% and 75%, each for 5 min; washing 3 times with PBS for 5 min each time.

4.4.2. Microwave antigen retrieval: immersing the sections in 0.01 M citrate buffer (pH 6.0), heating to boiling in a microwave oven, and repeating twice; after natural cooling, washing twice with PBS for 5 min each time.

4.4.3. Incubating in 0.3% Triton-100 for 10 min at room temperature, and washing 3 times with PBS for 5 min each time.

4.4.4. Blocking endogenous peroxidase: blotting around the brain tissue with filter paper, outlining the brain tissue with a PAP pen. Adding dropwise the peroxidase blocker, incubating for 10 min at room temperature, and washing 3 times with PBS for 5 min each time.

4.4.5. Adding dropwise normal serum blocking solution, keeping at 37° C. for 30 min, shaking off the excess liquid and not washing.

4.4.6. Adding dropwise the primary antibody diluted with 0.01 M PBS, keeping at 4° C. overnight; washing 3 times with PBS for 10 min each time.

4.4.7. Adding dropwise Fluorescein (FITC)-conjugated Affinipure Goat Anti-Mouse 1 gG (H+L) diluted with 0.01M PBS at a ratio of 1:100 and CY3-conjugated Affinipure Goat Anti-Rabbit 1 gG (H+L) diluted with 0.01M PBS at a ratio of 1:100, and washing 5 times with PBS for 5 min each time at 37° C.

4.4.8. Sealing with water-soluble sealant. Observing by laser confocal microscopy.

5, Thioflavin-S Staining 5.1. Dewaxing the paraffin sections of the brain tissue and taken through graded alcohols to water;

5.2. Washing 3 times with PBS for 3 min each time;

5.3. Blocking endogenous peroxidase: blotting around the brain tissue with filter paper, outlining the brain tissue with a PAP pen; adding dropwise the peroxidase blocker, incubating for 10 min at room temperature, and washing 3 times with PBS for 3 min each time.

5.4. Incubating in the Thioflavin-S ethanol solution for 10 min in the dark.

5.5. Washing 3 times with the PBS on a shaker in a dark for 3 min each time; sealing with the water-soluble sealant, and observing by fluorescence microscope.

6. Statistical Methods

The experimental data is expressed as mean value±standard error ($\bar{x}\pm SD$). One-way ANOVA. or two-way ANOVA was performed using SPSS 17.0 software. $P<0.05$ was considered to be statistically significant.

B. Experimental Results

OAB-14 Promoted Clearance of β-Amyloid Protein:

OAB-14 reduced the deposition of the β-amyloid protein by 67.4% in the cerebral cortex and hippocampus of APP/PS1 double transgenic AD model mice aged 8 months old by continuous intragastric administration for 14 days at a dose of 200 mg/kg, and had a good dose-effect relationship in the dose range of 50-200 mg/kg. The mechanism of reducing β-amyloid plaques was not related to Aβ producing enzyme, but the mechanism is achieved by increasing the expression of the Aβ metabolizing enzymes NEP and IDE in the brain of the mice, promoting the phagocytosis of microglia in the central nervous system to β-amyloid protein and so forth.

OAB-14 Reduced Overphosphorylation of Tau Protein:

In physiological conditions, Wnt binded to frizzled protein to inhibit GSK-3β activity, thereby inhibiting tau phosphorylation to protect microtubule structure. Nerve growth factor could also inhibit the activity of GSK-3β through the PI3K/AKT pathway. However, in the presence of Aβ, Aβ competed with Wnt for binding to the frizzled protein, which abolished inhibition of GSK-3β and made tau overphosphorylate. The neurotoxicity of Aβ also reduced the expression of neurotrophic factors, thereby inhibiting the PI3K/AKT pathway and making tau protein phosphorylate. OAB-14 could abolish the inhibition of Aβ, thereby reducing the tau protein phosphorylation to protect neurotubulin and prevent neuronal tangle.

OAB-14 Improved Behavioral Disorders Such as Learning, Memory and Social Activities in Animals:

OAB-14 at a doge of 50, 100 and 200 mg/kg were respectively given to APP/PS1 double transgenic AD model mice aged 8 months by continuous intragastric administration for 14 days or 3 months (to 11 months old, equivalent to the middle- and late-aged AD), using donepezil as a positive control. The results showed that, whether administered for 14 days or for 3 months consecutively, OAB-14 could dose-dependently improve a variety of learning and memory disorders of the model animals in the new object discrimination test, the Y-maze test, the Morris water maze test, the nesting experiment and the social interaction experiment, and improve cognitive function, social interaction and self-care ability, showing a good dose-effect relationship, especially in the high-dose group, the effect was significantly stronger than that of the donepezil group and completely restored to the level of the blank control group.

OAB-14 Improved Pathological Abnormalities of Hippocampal Neurons in APP/PS1 Double Transgenic AD Model Mice:

The neurons in the hippocampal CA1 area of the blank control group had clear structures and was closely arranged, and no abnormalities were observed. The neurons of the mice in the model group were loosely arranged, had symptoms of edema, chromatin reduction, nuclear pyknosis, and the light staining or dissolution of cell body and cell nucleus were obversed. The neurons of mice in the 200 mg/kg OAB-14 group and the 100 mg/kg group were closely arranged, no visible edema and nuclear pyknosis, and the hippocampus was neat.

OAB-14 Improved Neuronal Ultrastructural Abnormalities in Hippocampal CA1 Region of the APP/PS1 Mice:

The results of transmission electron microscopy showed that the neuron nucleus in the blank control group were spherical, the nuclear membrane was intact, the nucleolus was clearly visible, the coloration was deep, and the mitochondrial outer membrane and crest were clear. The cytoplasm of the model group was largely dissolved and lost, and damage of many nuclear membranes, dissolution of some parts of the nuclear membrane, aggregation of the chromatin in the nucleus, and expansion of the rough endoplasmic reticulum into bubbles were observed; and most of the mitochondrial outer membranes were damaged and the crest was partially dissolved and blurred. OAB-14 significantly improved the ultrastructure of the neurons in a dose-dependent manner, especially in the 200 mg/kg OAB-14 group, the nuclear outline of the neurons was clear, the nuclear membrane was intact, the nucleus was spherical, the nucleolus was clear, the cytoplasm was abundant, and a large amount of ribose was present, the rough endoplasmic reticulum was nearly normal, and most of the mitochondrial outer membranes and crest are intact and only partially dissolved.

OAB-1.4 Significantly Improved the Ultrastructural and Functional Abnormalities of the Hippocampal Synapses in the APP/PS1 Mice:

The results of transmission electron microscopy showed that the structures of the pre-synaptic membranes and post-synaptic membranes of the hippocampus were clearly visible in the blank group, the number of synaptic vesicles in the anterior membrane was higher, the synaptic vesicles were clearly visible, and the post-synaptic membrane had deep stained dense spots. Compared with the blank control group, the number of synapses in the hippocampal CA1 region of the model group decreased, most of the synaptic clefts were stenosis, pre-synaptic membranes and post-synaptic membranes are fused, anterior membrane vesicles were reduced, and the density of part of post-synaptic membrane was reduced. The results of the Western blot showed that the expression of the synaptic-related protein such as SYP, PSD95 and GAP43 was significantly reduced. The results of the patch clamp experiment showed the LTP representing synaptic function was significantly reduced. The synaptic ultrastructures were significantly improved in the 100 mg/kg OAB-14 group and the 200 mg/kg OAB-14 group, which was shown that the synaptic cleft was clearly visible, there were more synaptic vesicles in the pre-synaptic membrane, pre-synaptic membranes and post-synaptic membranes were clear and uniform, and the post-synaptic dense spots were deeply stained, the expression of the synaptic-related proteins such as SYP, PSD95 and GAP43 was significantly increased, and LTP was significantly enhanced.

Preliminary Evaluation of Safety:

The mice were intragastrically administrated with OAB-14 at a dose of 5000 mg/kg for LD50 test. No adverse reactions of the mice were observed with the naked eye, the mice were in good condition and no mice died, and no abnormalities were detected in organs such as heart, liver, spleen and kidney. In the behavioral experiment of improving learning and memory by administration for 3 consecutive months, all the experimental mice in the groups of low, medium and high dose of OAR-14 were in good condition, the hair was shiny and supple, and the index of the organ such as heart, liver, spleen and kidney was not seen to be abnormal.

Water Maze Oriented Navigation Experiment:

Compared with the blank control group, the escape latency of the mice in the model group trained on the second day was significantly increased, and the escape latency and total swimming distance trained on the third and fourth days were significantly increased. Compared with the model group, the 200 mg/kg OAB-14 group showed a significant decrease in the escape latency from the second day, and a significant decrease in the total swimming distance from the third day, the escape latency of the third and fourth days in the bexarotene group and the 100 mg/kg OAB-14 group were significantly reduced, and the total swimming distance of the fourth day in the 100 mg/kg OAB-14 group was significantly reduced.

The above experimental results indicated that OAB-14 significantly improved the spatial learning and memory disorders of the APP/PS1 mice.

Results of the Exploration Experiment:

The experimental results showed that compared with the blank control group, the swimming time in the target quadrant, the percentage of the swimming distance in the target quadrant and the number of the times traversing the safe platform were significantly reduced in the model group. Compared with the model group, the swimming time in the target quadrant, the percentage of the swimming distance in the target quadrant and the number of the times traversing safe platform were significantly increased in the bexarotene group, the 200 mg/kg OAB-14 group and the 100 mg/kg OAB-14 group.

Social Interaction Experiment:

The experimental results showed that: Compared with the blank control group, the active contact time of the model group was significantly reduced. Compared with the model group, the active contact time of the 200 mg/kg OAB-14 group was significantly increased.

Nesting Experiment:

The experimental results showed that: Compared with the blank control group, the nesting ability of the model group was significantly reduced at 12 h and 24 h; Compared with the model group, the nesting ability of the 200 mg/kg OAB-14 group was significantly increased at 6 h, 12 h and 24 h, and the nesting ability of the 100 mg/kg bexarotene group, the 1.3 mg/kg donepezil group and the 100 mg/kg OAB-14 was significantly increased at 12 h.

The invention claimed is:

1. An octahydroanthracene compound or pharmaceutically acceptable salts of the octahydroanthracene compound, wherein structural formulas of the octahydroanthracene compound are shown in (I) or (II):

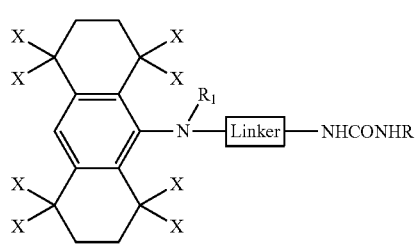
(I)

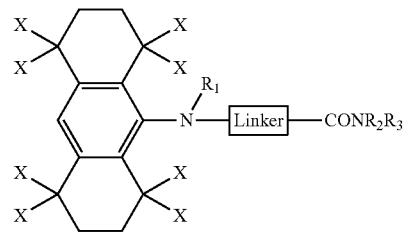
(II)

wherein X is H or C1-C6 alkyl group;

Linker is a substituted or unsubstituted C6-C10 aroyl or heteroaroyl group; wherein a substituent of the substituted C6-C10 aroyl or heteroaroyl group is a C1-C6 alkyl group, a C1-C6 alkoxy group, a halogen, an amino group, a nitro group, a mercapto group, a thioether, a sulfone, a sulfoxide or an aminoalkoxy group; or the Linker is a substituted or unsubstituted phenyl group, pyridine, furan, pyrrole thiazole or thiophene; wherein a substituent of the substituted phenyl group, pyridine, furan, pyrrole, thiazole or thiophene is a C1-C6 alkyl group or a C1-C6 alkoxy group;

$R_1$ is hydrogen or C1-C6 alkyl group;

R is a nitrogen- or nitrogen-free structural fragment;

$R_2$, $R_3$ are hydrogen, nitrogen- or nitrogen-free structural fragments;

and wherein the nitrogen-free structural fragment is C1-C20 alkyl group;

a structure of the nitrogen-structural fragment is:

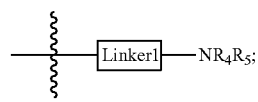

wherein the Linker1 of the structure of the nitrogen-structural fragment is a C2-C6 linear or branched alkyl group, and the $NR_4R_5$ is a primary amine or secondary amine.

2. The octahydroanthracene compound or the pharmaceutically acceptable salts of the octahydroanthracene compound of claim 1, wherein the nitrogen-free structural fragment is C1-C10 alkyl group.

3. The octahydroanthracene compound or the pharmaceutically acceptable salts of the octahydroanthracene compound of claim 1, wherein the $NR_4R_5$ is selected from the group consisting of:

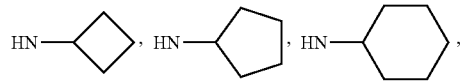

-continued

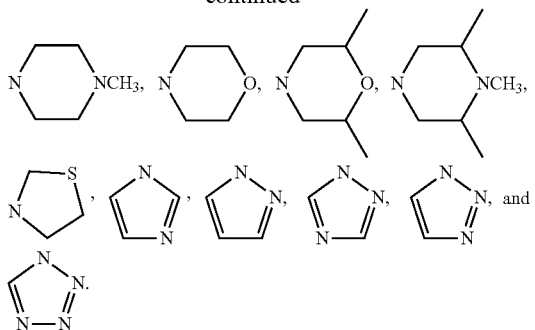

4. The octahydroanthracene compound or the pharmaceutically acceptable salts of the octahydroanthracene compound of claim 1, wherein X is hydrogen, methyl or ethyl.

5. An octahydroanthracene compound or pharmaceutically acceptable salts of the octahydroanthracene compound, selecting from:
4-[(1,1,4,4,5,5,8,8-octamethyl-1,2,3,4,5,6,7,8-octahydro-9-anthryl) carbamoyl] methyl benzoate;
4-[(1,1,4,4,5,5,8,8-octamethyl-1,2,3,4,5,6,7,8-octahydro-9-anthryl) carbamoyl] benzoic acid;
N-hydroxy-4-[(1,1,4,4,5,5,8,8-octamethyl-1,2,3,4,5,6,7,8-octahydro-9-anthryl) carbamoyl]benzamide;
N-(2-aminophenyl)-4-[(1,1,4,4,5,5,8,8-octamethyl-1,2,3,4,5,6,7,8-octahydro-9-anthryl) carbamoyl] benzamide;
N-[2-(N,N-diethylamino)]ethyl-4-[(1,1,4,4,5,5,8,8-octamethyl-1,2,3,4,5,6,7,8-octahydro-9-anthryl) carbamoyl] benzamide;
N-(2-amino) ethyl-4-[(1,1,4,4,5,5,8,8-octamethyl-1,2,3,4,5,6,7,8-octahydro-9-anthryl) carbamoyl] benzamide;
N-[2-(N,N-dimethyl amino)]ethyl-4-[(1,1,4,4,5,5,8,8-octamethyl-1,2,3,4,5,6,7,8-octahydro-9-anthryl) carbamoyl] benzamide;
N-(2-hydroxyphenyl)-4-[(1,1,4,4,5,5,8,8-octamethyl-1,2,3,4,5,6,7,8-octahydro-9-anthryl) carbamoyl] benzamide;
4-[(1,1,4,4,5,5,8,8-octamethyl-1,2,3,4,5,6,7,8-octahydro-9-anthryl) carbamoyl] aniline;
4-[(1,1,4,4,5,5,8,8-octamethyl-1,2,3,4,5,6,7,8-octahydro-9-anthryl) carbamoyl] ethyl phenylcarbamate;
4-[(1,1,4,4,5,5,8,8-octamethyl-1,2,3,4,5,6,7,8-octahydro-9-anthryl) carbamoyl]phenylcarbamoyl-1-morpholine;
1-(2-aminophenyl)-3-{4-[(1,1,4,4,5,5,8,8-octamethyl-1,2,3,4,5,6,7,8-octahydro-9-anthryl) carbamoyl] phenyl} urea;
1-(2-amino) ethyl-3-{4-[(1,1,4,4,5,5,8,8-octamethyl-1,2,3,4,5,6,7,8-octahydro-9-anthryl) carbamoyl] phenyl} urea;
1-(2-hydroxy) ethyl-3-{4-[(1,1,4,4,5,5,8,8-octamethyl-1,2,3,4,5,6,7,8-octahydro-9-anthryl) carbamoyl] phenyl} urea;
1-(3-hydroxy)propyl-3-{4-[(1,1,4,4,5,5,8,8-octamethyl-1,2,3,4,5,6,7,8-octahydro-9-anthryl) carbamoyl] phenyl} urea;
N,N-dimethyl sulfonyl-4-[(1,1,4,4,5,5,8,8-octamethyl-1,2,3,4,5,6,7,8-octahydro-9-anthryl) carbamoyl] aniline;
1-(4-carboxypropyl)-3-{4-[(1,1,4,4,5,5,8,8-octamethyl-1,2,3,4,5,6,7,8-octahydro-9-anthryl) carbamoyl] phenyl} urea;
N-{4-[(1,1,4,4,5,5,8,8-octamethyl-1,2,3,4,5,6,7,8-octahydro-9-anthryl) carbamoyl]phenylcarbamoyl}-4-piperidinyl formic acid;
4-[(1,1,4,4,5,5,8,8-octamethyl-1,2,3,4,5,6,7,8-octahydro-9-anthryl) carbamoyl] methyl phenylcarbamate;
1-(2-hydroxyphenyl)-3-{4-[(1,1,4,4,5,5,8,8-octamethyl-1,2,3,4,5,6,7,8-octahydro-9-anthryl) carbamoyl] phenyl} urea;
1-[2-(N,N-diethylamino)]ethyl-3-{4-[(1,1,4,4,5,5,8,8-octamethyl-1,2,3,4,5,6,7,8-octahydro-9-anthryl) carbamoyl] phenyl} urea;
1-[2-(N,N-dimethyl amino)]ethyl-3-{4-[(1,1,4,4,5,5,8,8-octamethyl-1,2,3,4,5,6,7,8-octahydro-9-anthryl) carbamoyl] phenyl} urea;
1-hydroxy-3-{4-[(1,1,4,4,5,5,8,8-octamethyl-1,2,3,4,5,6,7,8-octahydro-9-anthryl) carbamoyl]phenyl} urea; or
4-[(1,1,4,4,5,5,8,8-octamethyl-1,2,3,4,5,6,7,8-octahydro-9-anthryl) carbamoyl] phenyl carbamic acid-O-amino ester.

6. A pharmaceutical composition, comprising the octahydroanthracene compound or the pharmaceutically acceptable salts of the octahydroanthracene compound of claim 1.

7. A method of treating Alzheimer's disease, Parkinson's disease or tumors comprising administering the octahydroanthracene compound of claim 1 or a pharmaceutically acceptable salt thereof.

8. A method of treating Alzheimer's disease, Parkinson's disease or tumors comprising administering the pharmaceutical composition of claim 6.

9. A method for preparing the octahydroanthracene compound of claim 1, wherein: when X is a methyl group, a first starting material is 2,5-dimethyl-2,5-hexanediol, through chlorination, Friedel-Crafts alkylation, nitration, and reduction, amide is formed, hydrolysis is performed to re-form the amide, or after a first amide formation, reduction is performed to form urea, and a synthetic route of the octahydroanthracene compound is shown below:

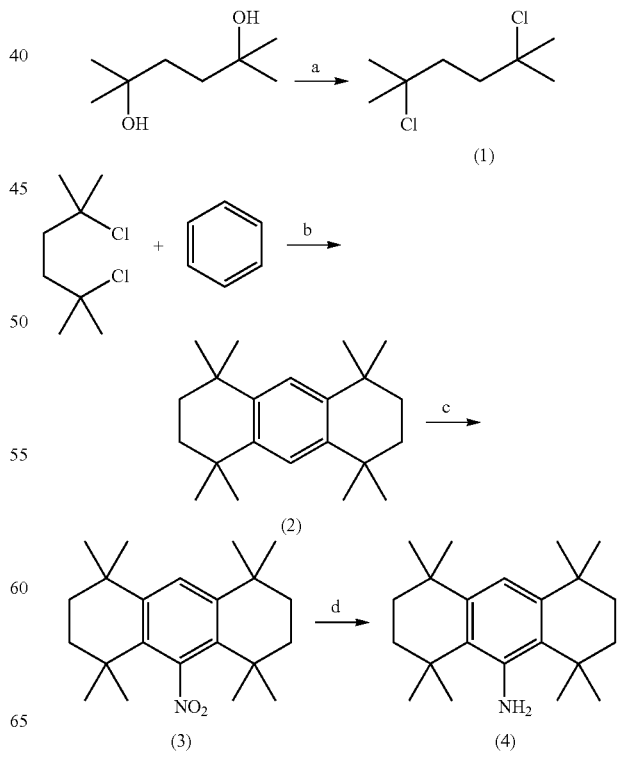

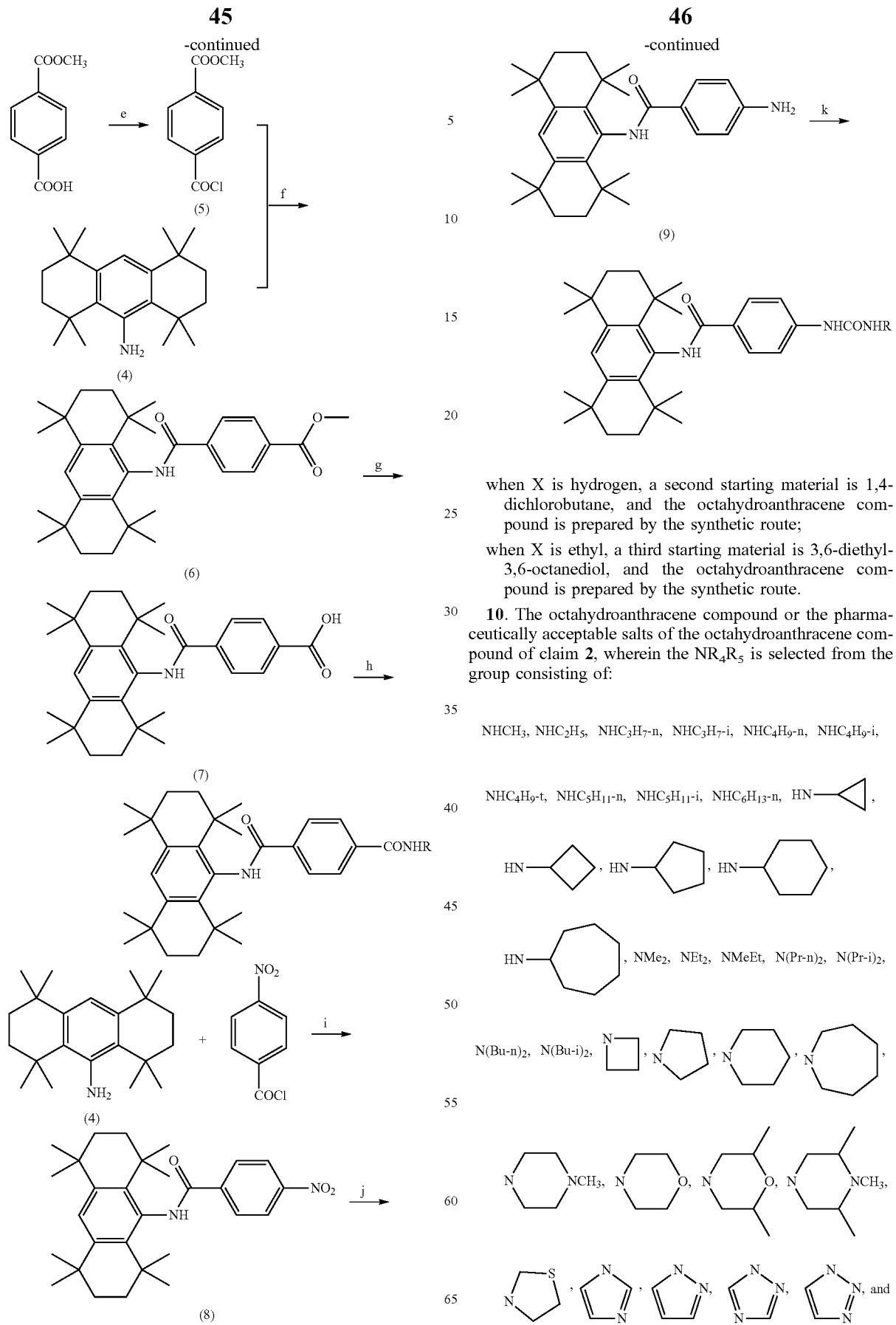

when X is hydrogen, a second starting material is 1,4-dichlorobutane, and the octahydroanthracene compound is prepared by the synthetic route;

when X is ethyl, a third starting material is 3,6-diethyl-3,6-octanediol, and the octahydroanthracene compound is prepared by the synthetic route.

10. The octahydroanthracene compound or the pharmaceutically acceptable salts of the octahydroanthracene compound of claim 2, wherein the $NR_4R_5$ is selected from the group consisting of:

$NHCH_3$, $NHC_2H_5$, $NHC_3H_7$-n, $NHC_3H_7$-i, $NHC_4H_9$-n, $NHC_4H_9$-i, $NHC_4H_9$-t, $NHC_5H_{11}$-n, $NHC_5H_{11}$-i, $NHC_6H_{13}$-n, HN—△,

HN—◻, HN—⬠, HN—⬡,

HN—⬢, $NMe_2$, $NEt_2$, NMeEt, $N(Pr-n)_2$, $N(Pr-i)_2$, $N(Bu-n)_2$, $N(Bu-i)_2$, and -continued

11. The octahydroanthracene compound or the pharmaceutically acceptable salts of the octahydroanthracene compound of claim 2, wherein X is hydrogen, methyl or ethyl.

12. The octahydroanthracene compound or the pharmaceutically acceptable salts of the octahydroanthracene compound of claim 3, wherein X is hydrogen, methyl or ethyl.

13. The pharmaceutical composition of claim 6, wherein: the nitrogen-free structural fragment is C1-C10 alkyl group.

14. The pharmaceutical composition of claim 6, wherein: the $NR_4R_5$ is selected from the group consisting of:

$NHCH_3$, $NHC_2H_5$, $NHC_3H_7$-n, $NHC_3H_7$-i, $NHC_4H_9$-n, $NHC_4H_9$-i, $NHC_4H_9$-t, $NHC_5H_{11}$-n, $NHC_5H_{11}$-i, $NHC_6H_{13}$-n, 

-continued

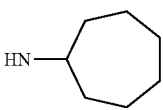, $NMe_2$, $NEt_2$, $NMeEt$, $N(Pr-n)_2$, $N(Pr-i)_2$,

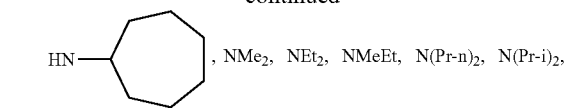

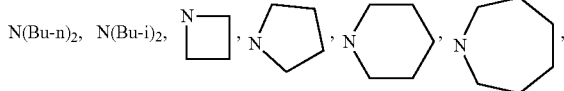

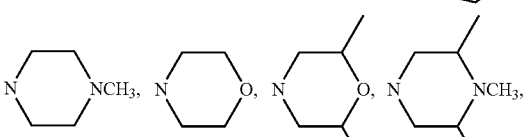

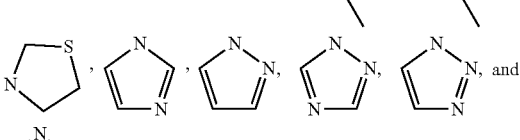

* * * * *